(12) United States Patent
Shukla

(10) Patent No.: US 9,718,842 B1
(45) Date of Patent: Aug. 1, 2017

(54) SILVER ION CARBOXYLATE PRIMARY ALKYLAMINE COMPLEXES

(71) Applicant: Eastman Kodak Company, Rochester, NY (US)

(72) Inventor: Deepak Shukla, Webster, NY (US)

(73) Assignee: EASTMAN KODAK COMPANY, Rochester, NY (US)

( * ) Notice: Subject to any disclaimer, the term of this patent is extended or adjusted under 35 U.S.C. 154(b) by 0 days.

(21) Appl. No.: 15/231,837

(22) Filed: Aug. 9, 2016

(51) Int. Cl.
C07F 1/10 (2006.01)
C07F 1/00 (2006.01)
G03F 7/06 (2006.01)

(52) U.S. Cl.
CPC ............... *C07F 1/00* (2013.01); *G03F 7/063* (2013.01)

(58) Field of Classification Search
CPC ............ C07F 1/00; C07F 1/10; G03F 7/063
USPC ........................................................ 556/116
See application file for complete search history.

(56) References Cited

U.S. PATENT DOCUMENTS

| | | | |
|---|---|---|---|
| 5,491,059 A | 2/1996 | Whitcomb | |
| 5,534,312 A | 7/1996 | Hill et al. | |
| 5,705,661 A | 1/1998 | Iwakura et al. | |
| 6,106,906 A * | 8/2000 | Matsuda ........... | G02F 1/133711 427/126.1 |
| 6,468,521 B1 | 10/2002 | Pedersen et al. | |
| 7,270,694 B2 | 9/2007 | Li et al. | |
| 7,306,969 B2 | 12/2007 | Wu et al. | |
| 7,494,608 B2 | 2/2009 | Li et al. | |
| 7,559,970 B2 | 7/2009 | Kim et al. | |
| 7,628,840 B2 | 12/2009 | Atsuki et al. | |
| 7,737,497 B2 | 6/2010 | Li | |
| 7,919,015 B2 | 4/2011 | Li et al. | |
| 8,163,073 B2 | 4/2012 | Chan et al. | |
| 8,226,755 B2 | 7/2012 | Chung et al. | |
| 8,298,314 B2 | 10/2012 | Li | |
| 8,419,822 B2 | 4/2013 | Li | |
| 9,188,861 B2 | 11/2015 | Shukla et al. | |
| 9,207,533 B2 | 12/2015 | Shukla et al. | |
| 2005/0129843 A1 | 6/2005 | Wu et al. | |

(Continued)

FOREIGN PATENT DOCUMENTS

WO WO2014/070131 A1 5/2014

OTHER PUBLICATIONS

Koen Binnemans et al., "Structure and Mesomorphism of Silver Alkanoates," Chem. Mater. 2004, 16. 2021-2027.

(Continued)

*Primary Examiner* — Porfirio Nazario Gonzalez
(74) *Attorney, Agent, or Firm* — J. Lanny Tucker

(57) ABSTRACT

A non-hydroxylic-solvent soluble silver complex has a reducible silver ion complexed with an α-oxy carboxylate and a primary alkylamine. This non-hydroxylic-solvent soluble silver complex can be represented by the following formula (I):

$$(Ag^+)_a(L)_b(P)_c \qquad (I)$$

wherein L represents the α-oxy carboxylate; P represents the primary alkylamine; a is 1 or 2; b is 1 or 2; and c is 1, 2, 3, or 4, provided that when a is 1, b is 1, and when a is 2, b is 2. Such complexes can be incorporated into photosensitive compositions that are then used to provide photosensitive thin films or photosensitive thin film patterns. The reducible silver ions can be quickly and efficiently reduced to electrically-conductive silver metal upon exposure to UV-visible radiation in various methods.

17 Claims, 3 Drawing Sheets

(56) References Cited

U.S. PATENT DOCUMENTS

| | | |
|---|---|---|
| 2006/0254387 A1 | 11/2006 | Lee et al. |
| 2007/0003603 A1 | 1/2007 | Karandikar et al. |
| 2007/0099357 A1 | 5/2007 | Li et al. |
| 2010/0021704 A1 | 1/2010 | Yoon et al. |
| 2015/0004325 A1 | 1/2015 | Walker et al. |

OTHER PUBLICATIONS

Edward Szlyk et al., "CVD of $Ag^I$ Complexes with Tertiary Phosphines and Perfluorinated Carboxylates—A New Class of Silver Precursors," Chem. Vap. Deposition 2001, 7, No. 3, 111-116.

Lin Song et al., "$[(CO)_3 (PPh_3)_2 OsAg(O_2 CCF_3)]$: A Model for an Intermediate on the Reaction Coordinate in Electron Transfer," Angew. Chem. Int. Ed. Engl. 31 (1992) No. 6, 770-772.

C. Oldham, "Complexes of Simple Carboxylic Acids," Prog. Inorg. Chemistry, 10, 233, 1968, 223-259.

\* cited by examiner

SILVER ION CARBOXYLATE PRIMARY ALKYLAMINE COMPLEXES

RELATED APPLICATIONS

Reference is made to the following commonly assigned and copending patent application, the disclosures of all of which are incorporated herein by reference:

U.S. Ser. No. 15/231,804 (filed on Aug. 9, 2016, by Shukla) and entitled "Silver Ion Carboxylate N-heteroaromatic Complexes";

U.S. Ser. No. 15/231,811 (filed on Aug. 9, 2016, by Shukla) and entitled "Photosensitive Reducible Silver Ion-Containing Compositions";

U.S. Ser. No. 15/231,815 (filed on Aug. 9, 2016, by Shukla, Lenhard, Mis, and Donovan) and entitled "Methods for Forming and Using Silver Metal";

U.S. Ser. No. 15/231,823 (filed on Aug. 9, 2016, by Shukla, Mis, Welter, Klubek, and Donovan) and entitled "Articles Having Reducible Silver Ion Complexes or Silver Metal";

U.S. Ser. No. 15/231,847 (filed on Aug. 9, 2016, by Shukla) and entitled "Photosensitive Reducible Silver Ion-Containing Compositions";

U.S. Ser. No. 15/231,852 (filed on Aug. 9, 2016, by Shukla, Lenhard, Mis, and Donovan) and entitled "Methods for Forming and Using Silver Metal"; and U.S. Ser. No. 15/231,857 (filed on Aug. 9, 2016, by Shukla, Mis, Welter, and Donovan) and entitled "Articles with Reducible Silver Ions or Silver Metal."

FIELD OF THE INVENTION

This invention relates to non-hydroxylic-solvent soluble silver complexes that can be incorporated into photosensitive reducible silver ion-containing compositions that can be used to provide electrically-conductive silver metal upon irradiation for a variety of uses. Each of these complexes includes a reducible silver ion complexed with both an α-oxy carboxylate and a primary alkylamine.

BACKGROUND OF THE INVENTION

It is well known that silver as a precious metal has desirable electrical and thermal conductivity, catalytic properties, and antimicrobial behavior. Thus, silver and silver-containing compounds have been widely used in alloys, metal plating processes, electronic devices, imaging sciences, medicine, clothing or other fibrous materials, and other commercial and industrial articles and processes to take advantage of silver's beneficial properties.

For example, silver compounds or silver metal have been described for use as metallic patterns or electrodes in metal wiring patterns, printed circuit boards (PCB's), flexible printed circuit boards (FPC's), antennas for radio frequency identification (RFID) tags, plasma display panels (PDP's), liquid crystal displays (LCD's), organic light emitting diodes (OLED's), flexible displays and organic thin film transistors (OTFT's), among other electronic devices known in the art.

Rapid advances are also occurring for making and using various electronic devices for various communication, financial, and archival purposes.

Silver is an ideal conductor having electrical conductivity 50 to 100 times greater than indium tin oxide that is commonly used today in many devices. For example, the art has described the preparation of electrically-conductive films by forming and developing (reducing) a silver halide image in "photographic" silver halide emulsions through an appropriate mask to form electrically-conductive grid networks having silver wires having average sizes (width and height) of less than 10 μm and having appropriate lengths. Various efforts have been made to design the silver halide emulsions and processing conditions to optimize electrically-conductive grid designs.

While silver as an electrical conductor has a wide range of potential uses in the field of printed electronics, the microfabrication of electrically-conductive tracks (grids, wires, or patterns) by photolithographic and electroless techniques is time consuming and expensive, and there is an industrial need for direct digital printing to simplify the processes and to reduce manufacturing costs.

Furthermore, it is desirable to fabricate silver-containing electronics onto polymeric or similar temperature-sensitive substrates by solution-based printing processes. Metallic electrically-conductive wires or grids of low resistance must be achieved at sufficiently low temperatures so as to be compatible with organic electronics on polymeric substrates. Among various known methods for fabricating electrically-conductive silver grids or patterns, the direct printing of silver-containing inks provides attractive prospects for making such electrically-conductive patterns.

Commonly used silver-conductive inks useful for this purpose are currently based or dependent upon the presence of silver nanoparticle (NP) solutions or dispersions, all of which have associated drawbacks. To overcome the common problem of aggregation and flocculation in silver nanoparticle based inks, various thiolate encapsulating surfactants or dispersants can be used. Volkman et al. [*Chem. Mater.* 23, 4634-4640 (2011)] observed that a thiolate encapsulating surfactant could be used to treat 3 nm silver particles in silver-containing inks to achieve films sintered at temperatures above 175° C. in air. Sintering is essential to obtain the electrical conductivities required for electronic applications. The effects of sintering on electrical performance and microstructure for an inkjet-printed copper nanoparticle ink were explored by Niittynen et al. [*Sci. Rep.* 5, article number: 8832 (2015)]. These workers used laser and intense pulsed light (IPL) sintering in order to obtain articles having electrical conductivities greater than 20% of that of bulk copper.

However, sintering techniques have major disadvantages. In many cases, sintering steps require high temperatures that are not compatible with polymer substrates such as polyethylene terephthalate or polycarbonate that are commonly employed in many consumer electronic articles. Furthermore, the metal-containing inks used for these processes have disparate viscosities and synthetic parameters. Particle-based inks typically contain electrically-conductive metal particles that are synthesized separately and then incorporated into an ink formulation. Each resulting particle-based ink must then be optimized for use in a specific printing process.

Grouchko et al. [*ACS Nano* 5(4) 3354-3359 (2011)] recently overcame some of these problems by employing a room temperature, "built in" sintering mechanism that successfully produced silver metal articles exhibiting electrical conductivities as high as 41% of the electrical conductivity of bulk silver. To obtain these electrical conductivity values, a chloride salt (such as NaCl) or HCl vapor was employed to strip a polymeric (polyacrylic acid sodium salt) electrosterically stabilizing coating from the ~15 nm diameter silver nanoparticle feedstock. This sintering mechanism consisted of spontaneous coalescence and Ostwald ripening, driven by the surface-to-volume energy of the very small silver nanoparticles. Thus, all of these nanoparticle-based processes inherently involve sintering processes, whether they are chemical (for example using a strong acid such as hydrochloric acid), thermal, laser, or UV activated.

Inkjet printing and flexographic printing have also been proposed for providing patterns of silver or silver-containing compounds, requiring the careful fabrication of a silver-containing paste or "ink" with desirable surface tension, viscosity, stability, and other physical properties required for such application processes. High silver content has generally been required for high electrical conductivity, and calcination or sintering may be additionally required for increasing electrical conductivity of printed silver inks.

An alternative to the approaches described above is to employ a chemical ink formulation where the silver source is a molecular precursor or cation (such as a silver salt) that is then chemically reacted (or reduced) to produce silver metal. Electrically-conductive inks that are in the form of a chemical solution rather than as a suspension or dispersion of metal particles, have gained interest in recent years [see for example Walker and Lewis in *J. Am. Chem. Soc.* 134, 1419 (2012); and Jahn et al. *Chem. Mater.* 22, 3067-3071 (2010)]. One conductive ink of this type is known as a Metalorganic Decomposition (MOD) variety ink, for example, as described by Jahn et al. [*Chem. Mater.* 22, 3067-3071 (2010)] who investigated silver printing using an aqueous transition metal complex [$AgO_2C(CH_2OCH_2)_3H$]-containing MOD ink. They reported the formation of metallic silver features having electrical conductivities as high as $2.7 \times 10^7$ S m$^{-1}$, which corresponds to an electrical conductivity that is 43% of that of bulk silver, although a sintering temperature of 250° C. was required. MOD inks thus overcome some problems associated with the use of nanoparticle-containing inks, for example, nozzle clogging, but numerous printing passes are generally required to obtain an adequate sheet resistance. Post-treatment sintering processes are also still required to fully consolidate the electrically-conductive articles if the growth process is initiated from discrete nanoparticle intermediates, which is common in MOD ink processes.

U.S. Patent Application Publication 2015-0004325 (Walker et al.) describes a chemically-reactive silver ink composition comprised of a complex of a silver carboxylate salt and an alkylamine, in which the complex is used to form an electrically-conductive silver structure at a temperature of 120° C. or less. Unfortunately, even these temperatures render the ink incompatible with many polymeric and paper substrates used in flexible electronic and biomedical devices. Furthermore, since alkylamines are known to reduce silver at room temperature, long term stability of such compositions is tentative. The complexes must be kept in air-tight refrigerated storage for extended keeping stability (Column I, paragraph 0054 of the publication). Furthermore, the publication teaches long heating times were needed to obtain low resistivity in the resulting articles.

A common coordinating ion to form organic silver complexes is carboxylic acid [*Prog. Inorg. Chem.,* 10, 233 (1968)]. However, silver-carboxylate complexes are generally insoluble in organic solvents [see for example, U.S. Pat. No. 5,491,059 of Whitcomb and U.S. Pat. No. 5,534,312 of Hill et al.] and have a high decomposition temperature. To solve this problem, several methods have been proposed for example, in *Ang. Chem., Int. Ed. Engl.,* 31, p. 770 (1992), *Chem. Vapor Deposition,* 7, 111 (2001), *Chem. Mater.,* 16, 2021 (2004), and U.S. Pat. No. 5,705,661 (Iwakura et al.). Among such methods are those using silver carboxylates having long alkyl chains or including amine compounds or phosphine compounds. However, the silver complexes known thus far have insufficient stability or solubility and a high decomposition temperature is needed for pattern formation and are decomposed slowly.

Allegedly to address some of these problems, U.S. Pat. No. 8,226,755 (Chung et al.) describes silver complexes formed by reacting a silver compound (such as a silver salt) with an ammonium carbamate compound or ammonium carbonate compound. Moreover, U.S. Patent Application Publication 2010/0021704 (Yoon et al.) describes the preparation and use of fatty acid silver salts complexed with amines and in admixture with silver oxide to form silver metal from the silver oxide at low temperature.

U.S. Pat. No. 8,163,073 (Chan et al.) describes the use of silver ammonium complex ions, silver amine complex ions, silver-amino acid complex ions, silver halide complex ions, silver sulfite complex ions, or silver thiosulfate complex ions for silver plating processes to form silver wires for various devices.

U.S. Pat. No. 7,682,774 (Kim et al.) describes other photosensitive compositions comprising silver fluoride-organic complex precursors as catalyst precursors as well as the use of polymer derived from a monomer having a carboxyl group and a co-polymerizable monomer that may provide polymeric stability and developability of the resulting "seed" silver catalyst particles used for electroless plating.

U.S. Pat. No. 8,419,822 (Li) describes a process for producing carboxylic acid-stabilized silver nanoparticles by heating a mixture of a silver salt, a carboxylic acid, and a tertiary amine. However, it has been observed that such silver-containing complexes are not thermally or light stable. The reducible silver ions are readily reduced under ambient light conditions, and the resulting electrical conductivity of silver particles is minimal.

Other industrial approaches to preparing electrically-conductive films or elements have been directed to formulating and applying photocurable compositions containing dispersions of metal particles such as silver metal particles to substrates, followed by curing of the photocurable components in the photocurable compositions. The applied silver particles in the cured compositions thus act as catalytic (seed) particles for electrolessly plated electrically-conductive metals. Useful electrically-conductive grids prepared in this manner are described for example, in U.S. Pat. No. 9,188,861 (Shukla et al.) and U.S. Pat. No. 9,207,533 (Shukla et al.) and in US Patent Application Publications 2014/0071356 (Petcavich) and 2015/0125596 (Ramakrishnan at al.). Using these methods, photocurable compositions containing catalytic silver particles can be printed and cured on a suitable transparent substrate, for example a continuous roll of a transparent polyester, and then electroless plating can be carried out on the catalytic silver particles. However, these methods require that high quantities of silver particles be dispersed within the photocurable compositions in a uniform manner so that coatings or printed patterns have sufficiently high concentration of catalytic sites. Without effective dispersing, silver particles readily agglomerate, leading to less effective and uniform application of catalytic metal patterns and electroless plating.

Despite all of the various approaches and efforts to provide electrically-conductive silver in various consumer and industrial articles described above, there remains a need for photosensitive silver-generating compositions and processes which can rapidly generate metallic silver at room temperature. Ideally such photosensitive compositions should have several properties: stability at room temperature for an extended period of time (limited self-reduction of silver ions); capable of being deposited using a wide range of application processes, whether uniformly or patternwise; useful at room temperature; and controllable chemical activity.

SUMMARY OF THE INVENTION

The present invention provides a non-hydroxylic-solvent soluble silver complex comprising a reducible silver ion complexed with an α-oxy carboxylate and a primary alkylamine, the non-hydroxylic-solvent soluble silver complex being represented by the following formula (I):

$$(Ag^+)_a(L)_b(P)_c \qquad (I)$$

wherein L represents the α-oxy carboxylate; P represents the primary alkylamine; a is 1 or 2; b is 1 or 2; and c is 1, 2, 3, or 4, provided that when a is 1, b is 1, and when a is 2, b is 2.

The present invention is directed to novel non-hydroxylic-solvent soluble silver complexes, each complex comprising a silver ion complexed with one or more α-oxy carboxylate compounds and one or more primary alkylamines, and to uses of such complexes in photosensitive compositions and articles, and methods for producing and using same. For example, such novel complexes car be incorporated into silver "inks" or photosensitive reducible silver ion-containing compositions that can include a photosensitizer and a solvent medium comprising one or more non-hydroxylic solvents. When present, the photosensitizer upon absorption of actinic radiation, decomposes the non-hydroxylic-solvent soluble silver complex to form electrically-conductive metallic silver in a rapid manner at room temperature. Reducible silver ions can be photochemically converted to silver metal without the photosensitizer being present but this usually happens at a significantly slower rate.

Such novel complexes described herein and photosensitive compositions containing same can be used in various methods comprising the silver "ink" as a uniform photosensitive thin film or as a photosensitive thin film pattern on a substrate, and exposing the applied material to suitable actinic radiation to generate electrically-conductive silver metal (uniform layer or pattern) at room temperature.

The present invention provides several important advantages over known technology.

Firstly, in the presence of an appropriate photosensitizer, upon absorption of actinic radiation the non-hydroxylic-solvent soluble silver complex according to the present invention herein rapidly generates electrically-conductive silver metal at room temperature. Thus, metallic silver generation is possible in a high speed, continuous manufacturing operations, such as roll-to-roll operations.

In addition, the complexes described herein and the photosensitive compositions into which they are incorporated according to this invention are stable at room temperature when kept in the dark or under yellow safe light conditions so that there is very little premature reduction of silver ion. Thus, the chemistry according to the present invention in such complexes and photosensitive compositions is highly controllable so that they do not prematurely degrade and can be used in a wide variety of operations.

Since metallic silver is generated at room temperature upon exposure to actinic radiation, the photosensitive compositions according to the present invention provide greater flexibility in choice of substrate used including plastics (polymers), metals, glass, and other materials that could be used in various end products or electronic devices.

Moreover, as the photosensitive compositions according to the present invention are generally in the form of clear liquids, it is possible to choose a wide array of deposition techniques when producing various articles and uses, including but not limited to flexographic printing, ink jet printing, screen printing, gravure printing, roll-to-roll coating, spraying, and other techniques that would be readily apparent to one skilled in the art.

The advantages described herein are achieved with the use of novel non-hydroxylic-solvent soluble silver complexes described herein. Each complex comprises at least one reducible silver ion that is complexed with an α-oxy carboxylate and a primary alkylamine. These non-hydroxylic-solvent soluble silver complexes are described in more detail below.

The provision of silver metal from the complexes according to the present invention can be carried out in one of two different photochemical processes, depending upon the type of photosensitizer that is present. In some embodiments, the photosensitizer is electron-accepting and upon excitation with photon captured from electromagnetic radiation, it reacts with the α-oxy carboxylate ion, but in other embodiments, the photosensitizer is electron-donating and upon excitation with photon captured from electromagnetic radiation, it reacts with the reducible silver ion.

Other advantages of the present invention would be readily apparent to one skilled in the art in view of the teaching provided herein.

DETAILED DESCRIPTION OF THE INVENTION

Figure 1:
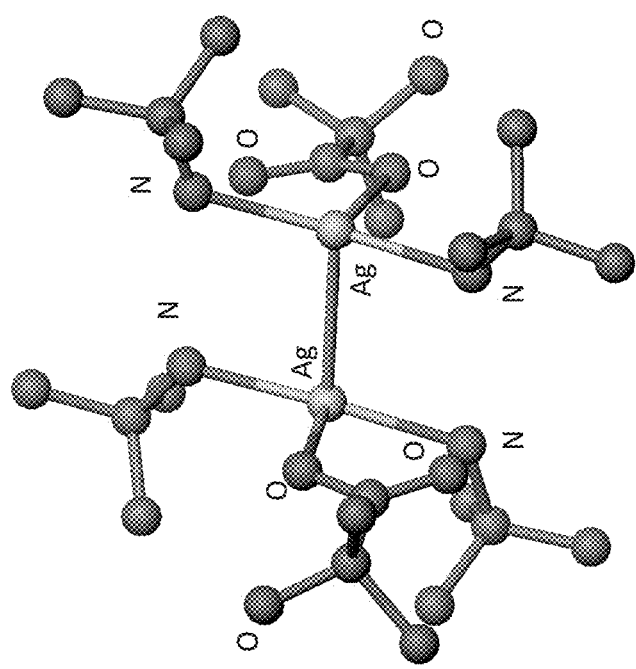
FIG. 1 is an illustration of the crystal structure of a silver ion-containing complex as described in Invention Example 4 below.

The following discussion is directed to various embodiments of the present invention and while some embodiments can be desirable for specific uses, the disclosed embodiments should not be interpreted or otherwise considered to limit the scope of the present invention, as claimed below. In addition, one skilled in the art will understand that the following disclosure has broader application than is explicitly described in the discussion of any embodiment.

Definitions

As used herein to define various components of the photosensitive reducible silver ion-containing compositions, photosensitive thin films, photosensitive thin film patterns, or other materials used in the practice of the present invention, unless otherwise indicated, the singular forms "a," "an," and "the" are intended to include one or more of the components (that is, including plurality referents).

Each term that is not explicitly defined in the present application is to be understood to have a meaning that is commonly accepted by those skilled in the art. If the construction of a term would render it meaningless or essentially meaningless in its context, the term should be interpreted to have a standard dictionary meaning.

The use of numerical values in the various ranges specified herein, unless otherwise expressly indicated otherwise, are considered to be approximations as though the minimum and maximum values within the stated ranges were both preceded by the word "about." In this manner, slight variations above and below the stated ranges may be useful to achieve substantially the same results as the values within the ranges. In addition, the disclosure of these ranges is intended as a continuous range including every value between the minimum and maximum values as well as the end points of the ranges.

Unless otherwise indicated, the term "weight %" refers to the amount of a component or material based on the total amount of a photosensitive reducible silver ion-containing composition, formulation, solution. In other embodiments, "weight %" can refer to the % solids (or dry weight) of a dry layer, coating, thin film, silver wire, or silver pattern.

Unless otherwise indicated herein, the terms "non-hydroxylic-solvent soluble silver complex," "silver ion-containing complex," and "complex" refer to embodiments according to the present invention.

Unless otherwise indicated herein, the terms "photosensitive composition" and "photosensitive reducible silver ion-containing composition" refer to embodiments according to the present invention.

Unless otherwise indicated herein, "photosensitivity" refers to the ability for silver ions to be reduced to silver metal in a complex or photosensitive composition when irradiated with ultraviolet (UV) or visible radiation within the range of wavelengths of at least 150 nm and up to and including 750 nm, or particularly at least 190 nm and up to and including 450 nm. Thus, photosensitivity refers to either the complex directly absorbing radiation and undergoing photochemical reaction, or to a photosensitizer in the photosensitive composition absorbing actinic radiation and transferring energy to the complex via electron transfer to initiate the desired reaction.

Unless otherwise indicated, the term "non-aqueous" as applied to the photosensitive reducible silver ion-containing composition or solutions means that solvent media used to form such compositions or solutions are predominantly organic in nature and water is not purposely added but may be present in an amount of less than 10 weight %, or particularly less than 5 weight %, or even less than 1 weight %, of the total weight of all solvents in the solvent medium.

Average dry thickness of photosensitive thin films and silver metal-containing thin films described herein can be the average of at least 2 separate measurements taken, for example, using electron microscopy, optical microscopy, or profilometry.

Similarly, the average dry thickness or width of silver metal (including silver) lines, grid lines, or other silver metal-containing thin film pattern features described herein can be the average of at least 2 separate measurements taken, for example, using electron microscopy, optical microscopy, or profilometry.

The use of "dry" in reference to thickness and width refers to embodiments in which at least 50 weight % of originally present solvent(s) has been removed.

Unless otherwise indicated, the term "group" particularly when used to define a substituent or a moiety, can itself be substituted or unsubstituted (for example an "alkyl group" refers to a substituted or unsubstituted alkyl group) by replacement of one or more hydrogen atoms with suitable substituents (noted below) such as a fluorine atom. Generally, unless otherwise specifically stated, substituents on any "groups" referenced herein or where something is stated to be possibly substituted, include the possibility of any groups, whether substituted or unsubstituted, which do not destroy properties necessary for the utility of the component or non-aqueous metal catalytic composition. It will also be understood for this disclosure and claims that reference to a compound or complex of a particular general structure includes those compounds of other more specific formula that fall within the general structural definition. Examples of substituents on any of the mentioned groups can include known substituents such as: halogen (for example, chloro and fluoro); alkoxy, particularly those with 1 to 5 carbon atoms (for example, methoxy and ethoxy); substituted or unsubstituted alkyl groups, particularly lower alkyl groups (for example, methyl and trifluoromethyl), particularly either of those having 1 to 6 carbon atoms (for example, methyl, ethyl, and t-butyl); and other substituents that would be readily apparent in the art.

Unless otherwise indicated, all voltages described herein are measured versus SCE (saturated calomel electrode).

The term "non-hydroxylic" as used to define organic solvents used in the practice of the present invention refers to organic solvents from which hydroxy groups (—OH) are completely absent. Such non-hydroxylic solvents do not include water.

A protic solvent is a solvent that has a hydrogen atom bound to an oxygen atom (as in a hydroxyl group) or to a nitrogen atom (as in an amine group).

Uses

The deposition or patterning of functional electrodes, pixel pads, and conductive traces, lines and tracks, which meet electrical conductivity, processing, and cost requirements for practical applications have been a great challenge. Silver metal is of particular interest in electrically-conductive elements for electronic devices because silver is much lower in cost than gold and it possesses much better environmental stability than copper.

The inventive compositions of the present invention can be used for forming electrically-conductive metallic silver patterns and electrodes for example in membrane touch switches (MTS), battery testers, biomedical, electroluminescent lamps, radio frequency identification (RFID) antenna, flat panel displays such as plasma display panel (PDP) and organic light emitting diode (OLED) displays, printed transistors and thin film photovoltaics, and thereby reduce the numbers of steps for pattern formation in such devices.

The non-hydroxylic-solvent soluble silver complexes described herein have a number of actual and potential uses in various technologies and industries. Most specifically, they can be used to provide silver metal for various purposes, including but not limited to, the formation of electrically-conductive grids or patterns of fine wires or other geometric forms, the formation of silver seed particles for electroless plating with other electrically-conductive metals, and the formation of silver in various materials for antimicrobial activity.

More specifically, the non-hydroxylic-solvent soluble silver complexes described herein are particularly useful as part of photosensitive reducible silver ion-containing compositions that can be irradiated with UV or visible radiation of a chosen wavelength to provide silver metal as part of electrically-conductive metal patterns. These electrically-conductive metal patterns can be incorporated into various devices including but not limited to, touch screens or other transparent display devices, and in modern electronics such as solar cell electrodes, electrodes in organic thin film transistors (OTFTs), flexible displays, radio frequency identification tags, light antennas, and other devices that would be readily apparent to one skilled in the art from the teaching herein.

While it is not necessary to achieve exceptional advantages from use of the present invention, silver metal formed according to the present invention can also be used as catalytic sites for electrochemical plating using silver or other metals to improve electrically-conductivity of the resulting metal thin films or patterns.

Non-Hydroxylic-Solvent Soluble Silver Complexes

The inventive non-hydroxylic-solvent soluble silver complexes are designed with only three essential components: (1) one or two reducible silver ions complexed with both (2) one or two α-oxy carboxylate molecules, and (3) one, two, three, or four primary alkylamine molecules, all of which components are described below.

In general, each useful non-hydroxylic-solvent soluble silver complex can be represented by the following formula (I):

$(Ag^+)_a(L)_b(P)_c$     (I)

wherein L represents the α-oxy carboxylate; P represents the primary alkylamine; a is 1 or 2; b is 1 or 2; and c is 1, 2, 3, or 4, provided that when a is 1, b is 1, and when a is 2, b is 2.

In some embodiments:
(i) a and b are both 1 and c is 1 or 2;
(ii) a and b are both 2 and c is 2; or
(iii) a and b are both 2 and c is 4.

In addition, each non-hydroxylic-solvent soluble silver complex according to the present invention, has at minimum solubility in a non-hydroxylic solvent (as defined below) or at least 5 g/liter at atmospheric pressure and ambient temperature (15° C. to 25° C.). It is particular useful that this solubility feature is true in acetonitrile that is one of the more useful non-hydroxylic solvents.

In general, each non-hydroxylic-solvent soluble silver complex of formula (I) can be defined using oxidation potentials determined separately for the component parts, such that the "P" component that is a primary alkylamine having an oxidation potential of greater than 1.0 V. In many embodiments, the oxidation potential is greater than 1.2 V vs. SCE; the "L" component, that is, the α-oxy carboxylate, has a first oxidation potential of at least 1.0 V vs. SCE; and upon decarboxylation of the α-oxy carboxylate, a second radical is generated that has an oxidation potential of less than 1.0 V vs. SCE.

Further details of such properties are provided below.

It is very important that the non-hydroxylic-solvent soluble silver complexes according to this invention have significant stability over time in that each complex meets a silver ion stability test such that when the non-hydroxylic-solvent soluble silver complex is kept for 24 hours at ambient temperature (15-25° C.) and under yellow safelight, less than 0.1 mol % of the original silver ion content in the complex is reduced to silver metal (as tested by chemical analysis and UV-Vis absorption spectroscopy).

Silver (Ag) Ions:

Each of the non-hydroxylic-solvent soluble silver complexes according to the present invention comprises one or two reducible silver ions, that is, one or two $Ag^+$ or $Ag^{+1}$ ions, as a first essential component. Each reducible silver ion is complexed with one or two α-oxy carboxylate compounds. The complexation with an α-oxy carboxylate compound could be via two oxygen atoms provided from the same molecule of an α-oxy carboxylate compound, or oxygen atoms provided from two molecules of the same or different α-oxy carboxylate compounds.

In general, each non-hydroxylic-solvent soluble silver complex of formula (I) shown above can be defined using reduction potentials such that the $Ag^{+1}$ ion of the complex can have a reduction potential of less than 1.0 V vs. SCE; or the $Ag^{+1}$ ion of the complex can have a reduction potential of less than 0.5 V vs. SCE; or the $Ag^{+1}$ ion of the complex can have a reduction potential of less than 0 V vs. SCE.

Silver ions can be provided using any suitable silver salt, and as described below, they can be provided as part of a silver carboxylate salt in which the carboxylate is an α-oxy carboxylate [L component in formula (I)] according to the present invention.

α-Oxy Carboxylates:

A second essential component of the non-hydroxylic solvent-soluble complexes according to this invention includes one or more α-oxy carboxylate groups (moieties or components) in which the α-carbon atom attached directly to the carboxyl group [—C(=O)O—] has a hydroxy group, oxy, or an oxyalkyl substituent group. Thus, the α-oxy carboxylates can be either α-hydroxy carboxylates, α-alkoxy carboxylates, or α-oxy carboxylates. With the α-hydroxy carboxylates and α-alkoxy carboxylates, the remainder of the valences of that α-carbon atom can be filled with hydrogen or a branched or linear alkyl group (substituted or unsubstituted) as described below in more detail. The α-oxy carboxylates can be supplied to prepare the complexes as the corresponding free carboxylic acids or as corresponding alkali metal or ammonium salts.

In addition, the α-oxy carboxylate (L) generally has a molecular weight of 250 or less, or 150 or less, and it likely has a molecular weight of at least 75 and up to and including 150.

It is important to note that the carboxylate groups useful in the present invention are not simple alkyl and aryl carboxylates that lack the hydroxyl, alkoxy, or oxy group at the α-position.

In formula (I) shown above, b is 1 or 2, and in the embodiments where b is 2, the two α-oxy carboxylate compounds within a single complex molecule can be the same or different compounds. For example, the two α-oxy carboxylate compounds can be provided as two of the same molecules represented by either formula (II) or (II) as described below. Alternatively, the two α-oxy carboxylate compounds can be provided by two different molecules represented by formula (II), two different molecules represented by formula (III), or one molecule represented by formula (II) and one molecule represented by formula (III).

In some embodiments of the present invention, L of formula (I) described above can be represented by the following formula (II):

wherein $R_1$, $R_2$, and $R_3$ are independently hydrogen or branched or linear alkyl groups. In most embodiments, at least one of $R_1$ through $R_3$ is a branched or linear alkyl group having from 1 to 8 carbon atoms, and any of the hydrogen atoms in such branched or linear alkyl groups can be replaced with a heteroatom such as a fluorine atom substituent.

In particularly useful embodiments of formula (II), $R_1$ is hydrogen or a branched or linear alkyl group having 1 to 3 carbon atoms (that is, substituted or unsubstituted methyl, ethyl, n-propyl, and Iso-propyl), and $R_2$ and $R_3$ are independently branched or linear alkyl groups having 1 to 8 carbon atoms (including iso- and tertiary alkyl groups having 3 to 8 carbon atoms). In some embodiments, $R_2$ and $R_3$ are different branched or linear alkyl groups as defined above. In addition, any of the hydrogen atoms in any of the $R_1$, $R_2$, and $R_3$ branched or linear alkyl groups optionally can be replaced with a fluorine atom; for example, the terminal carbon atom of a branched or linear alkyl group can have 1 to 3 fluorine atoms.

Some particularly useful conjugate acids from which α-oxy carboxylates (L) of formula (II) can be selected from the group consisting of lactic acid, 2-hydroxybutyric acid, 2-hydroxy-3-methylbutyric acid, 2-hydroxy-3,3-dimethylbutyric acid, 2-hydroxy-isobutyric acid, 2-hydroxy-2-methylbutyric acid, 2-ethyl-2-hydroxybutyric acid, 2-hydroxy-2,3-dimethylbutyric acid, 2-ethyl-2-methoxybutyric acid, 2-methoxy-2-methylpropanoic acid, 1-hydroxycyclopentane-1-carboxylic acid, 2,3-dihydroxy-2,3-dimethylsuccinic acid, and 2,4-dihydroxy-2,4-dimethylpentanedioic acid. As noted above, mixtures of these materials can be used in a specific complex if desired.

In other embodiments of the present invention, L is represented in formula (I) by the following formula (III):

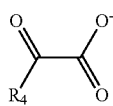

(III)

wherein $R_4$ is a branched or linear alkyl group having 1 to 8 carbon atoms, including branched iso- and tertiary alkyl groups having 3 to 8 carbon atoms. In addition, any of the hydrogen atoms in any of the branched or linear alkyl groups optionally can be replaced with a fluorine atom; for example, the terminal carbon atom of a $R_4$ branched or linear alkyl group can have 1 to 3 fluorine atoms.

Some useful conjugate acids from which the α-oxy carboxylate (L) represented by formula (III) can be selected from the group consisting of pyruvic acid, 3-methylpyruvic acid, 3,3-dimethylpyruvic acid, 3,3-dimethyl-2-oxobutanoic acid, 3,3-dimethyl-2-oxopentanoic acid, and 2,3-dioxosuccinic acid.

Some helpful understanding of the electrochemical behavior of the L groups in formula (I) is as follows in order to understand the scope of this essential component of the non-hydroxylic-solvent soluble silver complex.

Upon oxidation, the α-oxy carboxylate identified in formula (II) undergoes decarboxylation to produce a radical K• that can undergo further oxidation as shown in the following Equation (1):

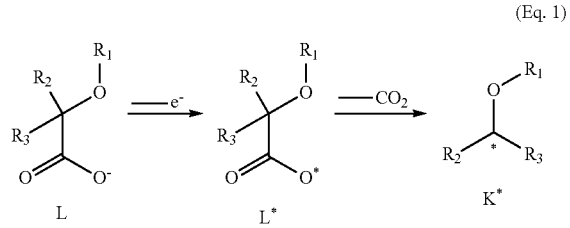

(Eq. 1)

As noted herein, the non-hydroxylic-solvent soluble silver complex according to this invention is characterized as having one or more molecules of two components complexed with the silver ion: namely the α-oxy carboxylate compound and a nitrogen-containing P compound as defined below. The chemical structural features of all of P, $R_1$, $R_2$, and $R_3$ determine the oxidation potential of L ($E_{ox1}$) whereas $R_1$, $R_2$, and $R_3$ determine the oxidation potential of the radical K• ($E_{ox2}$).

In accordance with the present invention, an α-oxy carboxylate compound of the complex is capable of transferring two electrons to the reducible silver ion. The first electron comes from oxidation of the α-oxy carboxylate to generate an α-oxy carboxyl radical L• that undergoes a bond cleavage reaction (decarboxylation) to give off $CO_2$ and to produce a second radical K• that can also desirably transfer a second electron to the reducible silver ion.

Thus, L can be a fragmentable α-oxy carboxylate wherein:

(1) L has a first oxidation potential of at least 1 V and up to and including 2 V (or for example, at least 1.2 V and up to and including 2 V);

(2) the oxidized form of L undergoes a bond cleavage reaction to provide the second radical K• and $CO_2$; and (3) the second radical K• has an oxidation potential ≤+1V (that is, equal to or more negative than +1V), and even less than or equal to 0.5V.

α-Oxy carboxylates that satisfy criteria (1) and (2) above but not criterion (3) are capable of donating one electron to the reducible silver ion and are referred to herein as "fragmentable one-electron donors". However, α-oxy carboxylates that meet all three criteria are capable of donating two electrons and are referred to herein as "fragmentable two-electron donors", and such components are particularly useful in the practice of the invention to provide faster reduction of the silver ions.

Fragmentation of the oxidized form of L that is, α-oxy carboxyl radical L•, is an important feature in the silver metal-producing methods according to the present invention. The kinetics of the fragmentation reaction can be measured by laser flash photolysis, a well-known technique used to study properties of transient species as described for example in "Absorption Spectroscopy of Transient Species", W. G. Herkstroeter and I. R. Gould in Physical Methods of Chemistry Series (2nd Ed.), Volume 8, 225-319, edited by B. Rossiter and R. Baetzold, John Wiley & Sons, New York, 1993. The rate constant of fragmentation of the α-oxy carboxylate radical is desirably faster than about $10^9$ per second (that is, the lifetime of the radical cation α-oxy carboxylate radical should be $10^9$ seconds or less). The fragmentation rate constants can be considerably higher than this, namely in the $10^2$ to $10^3$ $s^{-1}$ range. In particular, the fragmentation rate constant is desirably greater than $10^9$ $s^{-1}$ to and including $10^{13}$ $s^{-1}$, or from $10^{10}$ $s^{-1}$ to and including $10^{13}$ $s^{-1}$. Fragmentation rate constants for some carboxylate radicals are known in the literature [for example see, T. Michael Bockman, Stephan M. Hubig, and Jay K. Kochi, J. Org. Chem. 1997, 62, 2210-2221; James W. Hilborn and James A. Pincock, J. Am. Chem. Soc. 1991, 113, 2683-2686; Daniel E. Falvey and Gary B. Schuster, J. Am. Chem. Soc. 1986, 108, 1420-1422]. Fragmentation rate constants for some α-hydroxy carboxyl radicals have also been measured using laser flash photolysis and found to be very fast, that is $8 \times 10^{11}$ $s^{-1}$ (see, T. Michael Bockman, Stephan M. Hubig, and Jay K. Kochi, J. Org. Chem. 1997, 62, 2210-2221). Since fragmentation rates of simple alkyl and aryl carboxyl radicals are usually small (about $10^8$ to $10^9$ s$^{-1}$), such simple alkyl and aryl carboxylates are not useful in the practice of the present invention.

The ability of the second radical K• described above to reduce silver ion indicates that the oxidation potential of K• is nearly equal to or more negative than the reduction potential of silver ion in the complex. In some useful embodiments of the present invention, the second radical K•, resulting from the decarboxylation reaction has an oxidation potential equal to or more negative than −0.1 V or even more negative than −0.5 V. For example, this oxidation potential can be from −0.1 V to and including −2 V, or even from −0.5 V to and including −2 V, or more likely from −0.1 V to and including −1.0 V. In accordance with present invention, an α-oxy carboxylate ion that provides a second radical K• having an oxidation potential more negative than −0.1 V is particularly advantageous. All oxidation potentials are vs. SCE.

The oxidation potential of many such second radicals have been measured by transient electrochemical and pulse radiolysis techniques as reported by Wayner, D. D., McPhee, D. J., and Griller, D. in *J Am. Chem. Soc.* 1988, 110, 132; Rao, P. S. and Hayon, E. in *J. Am. Chem. Soc.* 1974, 96, 1287 and Rao, P. S, and Hayon, E. in *J. Am. Chem. Soc.* 1974, 96, 1295. The reported data demonstrate that the oxidation potentials of tertiary radicals are less positive (that is, the tertiary radicals are stronger reducing agents) than those of the corresponding secondary radicals, which in turn are more negative than those of the corresponding primary radicals.

Primary Alkylamines:

As noted above, in some embodiments of the non-hydroxylic solvent-soluble complexes, P is a primary alkylamine having a boiling point of less than or equal to 175° C., or having a boiling point of less than or equal to 125° C., or even at least 75° C. and up to and including 125° C., at atmospheric pressure. The useful primary alkyl amines that generally have a molecular weight of less than 500 and are thus considered "non-polymeric" as defined by molecular weight and boiling point.

The term "primary alkylamine" refers herein to compounds that are non-aromatic and are not cyclic in structure. They generally have a one or more nitrogen atoms as long as all other features (molecular weight, pKa, boiling point, and oxidation potential) described herein are met. In such compounds, each of the nitrogen atoms has two valences filled by hydrogen atoms and the remaining valence of each nitrogen atom is filled with a substituted or unsubstituted alkyl group (not including alkylaryl groups such as benzyl groups), or with a substituted or unsubstituted alkylene group for compounds defined herein as "primary alkyl diamines" that can be illustrated by the following formula (IV):

H$_2$N—R$_5$—NH$_2$ (IV)

wherein R$_5$ represents a substituted or unsubstituted, branched or linear, divalent alkylene group having 1 to 5 carbon atoms; and optional substituents include but are not limited to, fluoride atoms for any of the hydrogen atoms in the alkylene group.

In most useful embodiments, the primary alkyl amines comprise a single nitrogen atom and a single substituted or unsubstituted, branched or linear alkyl group having at least 3 carbon atoms, and generally from 3 to 6 carbon atoms, wherein any of the hydrogen atoms of the alkyl group can be replaced with a fluorine atom.

In general, each of such primary alkylamines has an oxidation potential greater than 1.0 V vs. SCE, or of at least 1.2 V vs. SCE.

Moreover, each of the useful primary alkylamines has a pKa of at least 1 and up to and including 30 as measured in acetonitrile, or more likely of at least 10 and up to and including 25 as measured in acetonitrile.

In some embodiments, the primary alkylamine has a pKa of at least 10 and up to and including 25 as measured in acetonitrile and an oxidation potential that is at least 2.0 V vs. SCE.

The useful primary alkylamines can be selected from the group consisting of a propylamine, n-butylamine, t-butylamine, isopropylamine, 2,2,2-trifluoroethylamine, 2,2,3,3,3-pentafluoropropylamine, 3,3,3-trifluoropropylamine, 1,2-dimethylpropylamine, t-amyl amine, and isopentylamine. Other useful primary alkylamines would be readily apparent to one skilled in the art. In some embodiments, the primary amine has an asymmetric carbon center on an alkyl chain. Some examples of such amines include but not limited to, a 2-amino-3-methylbutane, 3,3-dimethyl-2-butylamine, 2-aminohexane, sec-butylamine, and others that would be readily apparent to one skilled in the art from the foregoing description. Such primary alkylamines can be substituted with other groups that would be readily apparent to one skilled in the art.

In formula (I), when c is 2, 3, or 4, the primary alkyl amines can be the same or different molecules.

Useful primary alkyl amines can be readily obtained from various worldwide commercial sources of chemicals.

Method of Making Complexes

In general, the non-hydroxylic-solvent soluble silver complexes according to the present invention can be prepared by making a slurry of one or more silver α-oxy carboxylates in suitable solvent medium comprising one or more non-hydroxylic solvents (described below) at a general concentration of at least 0.1 mol/l and to and including 30 mol/l; and at room temperature, adding either one or more primary alkylamines gradually to obtain a clear solution in the resulting reaction solution. Specific details for these synthetic methods are provided below in the Examples.

Once prepared, the non-hydroxylic-solvent soluble silver complexes can be stored in the form of solid (after the solvent medium is removed by evaporative methods), or left in the reaction solution under conditions that are optimum for long-term stability (that is, negligible premature, non-photochemical reduction of silver ion to silver metal).

Some particularly useful non-hydroxylic-solvent soluble silver complexes prepared according to the present are represented by formula (I):

(Ag$^+$)$_a$(L)$_b$(P)$_c$ (I)

wherein:

a, b, and c are as defined above;

L has a molecular weight of 250 or less, and is represented by either of the following formula (II) or (III):

(II)

(III)

wherein R$_1$ is hydrogen or an alkyl group having 1 or 2 carbon atoms, R$_2$ and R$_3$ are independently branched or linear alkyl groups having 1 to 8 carbon atoms, wherein any of the hydrogen atoms in the alkyl groups can optionally be replaced with a fluorine atom, and $R_4$ is an alkyl group having 1 to 8 carbon atoms;

P is a primary alkylamine that is selected from the group consisting of propylamine, n-butylamine, t-butylamine, isopropylamine, 2,2,2-trifluoroethylamine, 2,2,3,3,3-pentafluoropropylamine, 3,3,3-trifluoropropylamine, 1,2-dimethylpropylamine, t-amyl amine, isopentylamine, 2-amino-3-methylbutane, 3,3-dimethyl-2-butylamine, 2-aminohexane, sec-butylamine.

Photosensitive Reducible Silver Ion-Containing Compositions

An important characteristic of the present invention is to ensure its general absorption and use in the UV to visible part of the electromagnetic spectrum. Ideally, irradiating energy should have wavelengths in the UV to visible region (for example 350 nm to 450 nm) to allow selective excitation of the photosensitizer in the presence of a large variety of chromophores.

The photosensitive reducible silver ion-containing compositions according to the present invention contain only two essential components for purposes of providing silver metal during photo-irradiation in a rapid manner: (a) one or more non-hydroxylic-solvent soluble silver complexes according to the present invention; and (b) a solvent medium comprising one or more non-hydroxylic solvents as described below. However, the presence of a third component, (c) one or more photosensitizers as described below, is very desirable in many embodiments, also can be considered essential to assure rapid photoreduction of silver ion at room or other low temperatures. No other components are purposely added to the photosensitive reducible silver ion-containing compositions according to the present invention so that the present invention provides simplified compositions that exhibit rapid silver metal formation for various methods and results. The incorporation of materials other than the three components (a) through (c) is likely to impede the generation of metallic silver.

The (a), (b), and (c) components can be put together in general by mixing them under "safe light" (yellow light) conditions if desired. This mixing can occur in suitable solvent medium (as described below) comprising one of more of the (b) solvents. The resulting photosensitive reducible silver ion-containing composition can be provided in liquid form having a viscosity of at least 1 centipoise and up to and including 1,000 centipoises at 25° C.

The one or more non-hydroxylic-solvent soluble silver complexes can be present in an amount of at least 5 weight % and up to and including 90 weight %, based on the total weight of the photosensitive reducible silver ion-containing composition.

Thus, in some embodiments, the photosensitive reducible silver ion-containing composition can comprise two or more different non-hydroxylic-solvent soluble silver complexes. Such embodiments can also include two or more different photosensitizers as described below.

The photosensitive reducible silver ion-containing composition of claim 1 has exceptive long term stability as demonstrated by a silver stability test such that when the photosensitive reducible silver ion-containing composition is held at ambient temperature (20° C. to 25° C.) and under yellow safelight for 24 hours, less than 0.1 mol % of its original silver ion content is reduced to silver metal.

Solvent Medium:

The essential non-hydroxylic-solvent soluble silver complex (and photosensitizer if present) are generally solubilized in a suitable solvent medium that is predominantly non-hydroxylic organic solvents that include but are not limited to, acetonitrile, benzonitrile, acetone, methyl ethyl ketone, butyronitrile, propylene carbonate, propionitrile, isovaleronitrile, valeronitrile, and a mixture of two or more thereof. It is also desirable that the non-hydroxylic solvents do not participate in any redox reaction. That is, such non-hydroxylic solvents should not be capable under general preparation, storage, and use conditions to reduce silver ion by transferring electrons or to oxidize an α-oxy carboxylate by accepting electrons. Such reactions by non-hydroxylic solvents would negatively impact the thermal stability of photosensitive compositions according to the present invention.

Water is not purposely added to the solvent medium, and if water is present, it should be present at no more than 5 weight % based on the total weight of the solvent medium (not including the non-hydroxylic-solvent soluble silver complex and photosensitizer).

Photosensitizers:

The photosensitizers useful in the present invention initiate the electrochemical transformation of the non-hydroxylic-solvent soluble silver complexes. The photosensitizer must be capable of either reducing the silver ions or oxidizing the α-oxy carboxylates after the photosensitizer has absorbed light (that is, photoinduced electron transfer) at an electromagnetic radiation having a wavelength of at least 150 nm and up to and including 700 nm. Thus, the photosensitive compositions according to this invention are generally sensitive to UV or visible electromagnetic radiation, or both, sufficient to convert the reducible silver ions in the non-hydroxylic reducible silver-containing complexes to silver metal. Such complexes containing reducible silver ions are inherently photosensitive to some degree but the presence of one or more photosensitizers as described herein enhances photosensitivity for much more effective and rapid reduction of reducible silver ions to silver metal. It is particularly useful to use photosensitizers that enhance sensitivity to electromagnetic radiation having a wavelength of at least 190 nm and up to and including 450 am, or even of at least 250 nm and up to and including 450 nm.

The amount of photosensitizer used in the photosensitive reducible silver ion-containing composition depends largely on its optical density and extinction coefficient at the wavelength(s) of radiation used to sensitize silver ion reduction. A photosensitizer with a low extinction coefficient can be utilized at relatively high levels and vice versa. Solubility of the photosensitizer can also be a factor in the amount that is used. In general, one or more photosensitizers described herein can be present in the photosensitive reducible silver ion-containing compositions in an amount of least 0.5 weight % and up to and including 4 weight %, or at least 1 weight % and up to and including 3 weight %, all amounts being based on the total weight of the one or more non-hydroxylic-solvent soluble silver complexes in the photosensitive reducible silver ion-containing composition. Thus, in some embodiments, two or more different photosensitizers can be used together.

There are two distinct classes of photosensitizers that can be used in the invention.

In some embodiments, the photosensitizers are electron-accepting photosensitizers that upon absorption of the incident radiation are capable of oxidizing the α-oxy carboxylate to initiate the reaction for silver ion reduction.

To determine whether a photosensitizer is capable of oxidizing the carboxylate ion in the non-hydroxylic solvent-soluble complex to a radical after the photosensitizer has absorbed suitable radiation, reaction energetics can be used.

There are four controlling parameters in these reaction energetics: (1) the excitation energy of an electron-accepting photosensitizer ($E_S^*$); (2) the reduction potential ($E_S^{red}$) of the electron-accepting photosensitizer (S); (3) the reduction potential ($E_{Ag^+}^{red}$) of the silver ion in the non-hydroxylic-solvent soluble complex; and (4) the oxidation potential ($E_C^{ox}$) of the α-oxy carboxylate in the complex (C) that is an electron donor. For these reactions to be energetically feasible, the energy of the excited state should be higher or only slightly lower than the energy stored in the primary product of initial electron transfer, the radical ion pair ($E_{1p}$), C•S+•.

The excitation energy of the electron-accepting photosensitizer (S) can be conveniently determined from the midpoint of the normalized absorption and emission spectrum of the compound, if the reaction proceeds from the singlet excited state. However, if the reaction proceeds via the triplet state, then the triplet energy of the electron-accepting photosensitizer can be used as the excitation energy.

The energy of the radical ion pair, $E_{1P}$, is given by Equation (2) below, where Δ is an energy increment that depends on the medium polarity and ranges from nearly zero in highly polar media to about 0.3 eV in the least polar media. The electrochemical measurements are carried out in polar solvents such as acetonitrile or methylene chloride.

$$E_{1P} = E_C^{ox} - E_S^{red} + \Delta \qquad \text{Equation (2).}$$

Thin photosensitive films according to the present invention are expected to be lower in dielectric constant, and as a result would not strongly solvate the radical ion pair. Thus, the energy increment Δ in Equation (1) noted above is expected to be near the maximum value, that is, in the range of 0.2 eV to 0.3 eV.

Accordingly, electron-accepting photosensitizers with an excitation energy equal to or larger than the difference between the oxidation potential of the α-oxy carboxylate in the complex (C) and the reduction potential of the electron-accepting photosensitizer ($E_C^{ox} - E_S^{red}$), will satisfy the energetic requirements of photoinitiating the reaction according to the following Equation (3):

$$E_S^* \geq E_C^{ox} - E_S^{red} + \Delta \qquad \text{Equation (3).}$$

Since the Δ value in the current system is expected to be in the range of from 0.2 eV to 0.3 eV, it is more convenient to express the energetic requirements of the electron-accepting photosensitizer relative to the donor in terms of a rearranged form in the following Equation (4):

$$E_S^* + E_S^{red} \geq E_C^{ox} \qquad \text{Equation (4).}$$

According to Equation (4), for the reaction to be energetically feasible, the algebraic sum of the excitation energy of the electron-accepting photosensitizer and its reduction potential should be approximately equal to or greater than the oxidation potential of the α-oxy carboxylate ion in the non-hydroxylic-solvent soluble silver complex (C).

In general, many different compounds can be used as electron accepting photosensitizers according to the present invention, provided that the energetic requirements discussed above are satisfied. Representative electron-accepting photosensitizers include but are not limited to, cyano-substituted aromatic carbocyclic compounds (such as 1-cyanonaphthalene, 1,4-dicyanonaphthalene, 9,10-dicyanoanthracene, 2,9,10-tricyanoanthracene, and 2,6,9,10-tetracyanoanthracene); aromatic anhydrides and imides (such as 1,8-naphthylene dicarboxylic, 1,4,6,8-naphthalene tetracarboxylic, 3,4-perylene dicarboxylic, and 3,4,9,10-perylene tetracarboxylic anhydride or imide); and condensed pyridinium salts (such as quinolinium, isoquinolinium, phenanthridinium salts; and pyrylium salts). Representative electron-accepting photosensitizers that involve the triplet excited state include but are not limited to, carbonyl compounds (such as quinones such as benzo-, naphtho-, and anthro-quinones having electron withdrawing substituents such as chloro or cyano groups). Ketocoumarins having strong electron withdrawing moieties such as a pyridinium group, are also useful as electron-accepting photosensitizers.

For the specific example of an α-oxy carboxylate, which has a peak oxidation potential of ~1.4 V vs. SCE, numerous electron-accepting photosensitizers that meet the requirement of the above Equation (3), can be used. For example, electron-accepting photosensitizers useful in the present invention include but are not limited to PS-1 through PS-8 in the following TABLE I.

TABLE I

| | | $E_{S^*}$ | $E_S^{red}$ |
|---|---|---|---|
| PS-1 | 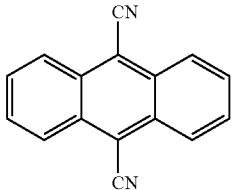 [SMILES: N#Cc1c2ccccc2c(C#N)c2ccccc12] | 2.92 | −0.91 |
| PS-2 | 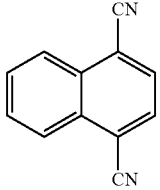 [SMILES: N#Cc1ccc(C#N)c2ccccc12] | 3.82 | −1.88 |
| PS-3 | 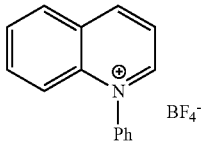 | 3.53 | −0.7 |
| PS-4 | 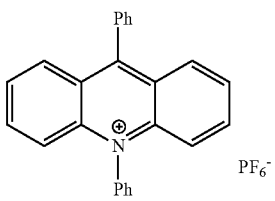 | 2.85 | −0.4 |
| PS-5 | 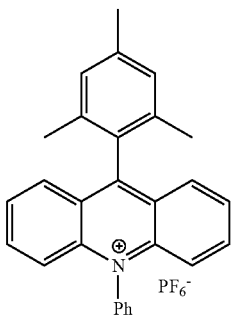 | 2.9 | −0.4 |

TABLE I-continued

| | | $E_{S^*}$ | $E_S^{red}$ |
|---|---|---|---|
| PS-6 | [tetrachloro-1,4-benzoquinone structure] | 2.13 | 0.0 |
| PS-7 | [3-(4-cyanobenzoyl)-5,7-dimethoxycoumarin structure] | 2.53 | −1.1 |
| PS-8 | [2,4,6-triphenylpyrylium tetrafluoroborate structure] | 3.1 | −0.29 |

In other embodiments of the present invention, upon absorption of noted electromagnetic radiation, the electron-donating photosensitizer (S) transfers an electron to the reducible silver ion in the non-hydroxylic-solvent soluble silver complex to form a photosensitizer radical cation (S⁺•) as shown in Equation (5) below, which in turn oxidizes the α-oxy carboxylate (L) to produce radical K• (see Equation (6) below). For photosensitizer radical cation (S⁺•) to be able to oxidize the α-oxy carboxylate (L), the oxidation potential of the electron donating photosensitizer (S) has to be greater than that of the α-oxy carboxylate.

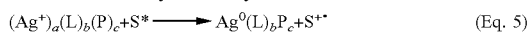

(Eq. 5)

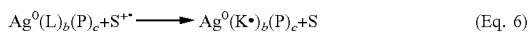

(Eq. 6)

To determine whether an electron-donating photosensitizer is capable of reducing the reducible silver ion after it has absorbed electromagnetic radiation, reaction energetics described above in Equations (2) and (3) can be used. Thus, for the reaction to be energetically feasible, the difference of electron-donating photosensitizer excitation energy and its oxidation potential should be approximately equal to or larger than the reduction potential of the silver ion in the complex ($E_{Ag+}^{red}$) [see Equation (7) below].

$$E_{S^*} - E_S^{ox} \geq -E_{Ag+}^{red} \qquad \text{equation (7)}$$

For the specific example of the reduction of reducible silver ion that has a peak reduction potential of −0.1 V vs. SCE, numerous electron-donating photosensitizers that meet the requirement of Equation (7) can be used.

The excitation energy of the electron-donating photosensitizer (S) is conveniently determined from the midpoint of its normalized absorption and emission spectrum if the reaction proceeds from the singlet excited state. However, if the reaction proceeds via the triplet state, then the triplet energy of the electron-donating photosensitizer should be used as the excitation energy.

In most embodiments, the electron-donating photosensitizer can be selected so that its oxidation potential is greater than that of α-oxy carboxylate. Some representative examples of such electron-donating photosensitizers, namely those having the difference of excitation energy and oxidation potential that is equal to or exceeds −0.1 V vs. SCE, include but not limited to, compounds PS-9 to PS-18 as shown in the following TABLE II.

TABLE II

| | | $E_{S^*}$ | $E_S^{ox}$ |
|---|---|---|---|
| PS-9 | [9,10-dimethoxyanthracene structure] | 3.2 | 0.98 |
| PS-10 | [pyrene structure] | 3.67 | 1.16 |
| PS-11 | [bis(5,7-dimethoxycoumarin-3-yl) ketone structure] | 2.43 | 1.77 |

TABLE II-continued

| | | $E_{S*}$ | $E_S^{ox}$ |
|---|---|---|---|
| PS-12 | [structure: 3-(4-cyanobenzoyl)-5,7-di-isopropoxycoumarin] | 2.52 | 1.77 |
| PS-13 | [structure: 3-(1-methylpyridinium-4-carbonyl)-5,7-dimethoxycoumarin, PF$_6^-$] | NA | NA |
| PS-14 | [structure: 3-(pyridine-4-carbonyl)-5,7-di-isopropoxycoumarin] | 2.42 | 1.8 |
| PS-15 | [structure: 3-(pyridine-3-carbonyl)-5,7-di-n-propoxycoumarin] | 2.42 | 1.8 |
| PS-16 | [structure: benzoxazolium cyanine dye with propylsulfonate, Ph substituents] | 3.3 | 1.3 |
| PS-17 | [structure: N,N'-diethyl benzoxazolium cyanine, PF$_6^-$] | 3.3 | 1.5 |
| PS-18 | [structure: N,N'-diethyl-5,5'-difluoro benzoxazolium cyanine, BF$_4^-$] | 3.4 | 1.5 |

NA means "not available".

Oxidation potentials for many electron-accepting and electron-donating photosensitizers are known and can be found, for example, in the *Encyclopedia of Electrochemistry of the Elements*, Organic Section, Volumes XI-XV, A. Bard and H. Lund (Editors) Marcel Dekkar Inc., NY (1984). If unavailable in the literature, oxidation potentials of useful electron-accepting and electron-donating photosensitizers can be measured by cyclic voltammetry using known equipment and procedures.

Thus, in some embodiments of the present invention, the photosensitizer is present, and when the photosensitizer is an electron-donating photosensitizer, it is defined by Equation (7) noted above, and when the photosensitizer is an electron-accepting photosensitizer, it is defined by Equation (4) noted above:

wherein:

$E_S^{ox}$ is the oxidation potential of the electron-donating photosensitizer;

$E_{S*}$ is the excitation energy of the electron-accepting photosensitizer;

$E_S^{red}$ is the reduction potential of the electron-accepting photosensitizer;

$E_{Ag+}^{red}$ is the reduction potential of the silver ion in the non-hydroxylic-solvent soluble silver complex; and $E_C^{ox}$ is the oxidation potential of the α-oxy carboxylate.

Precursor Articles

The non-hydroxylic-solvent soluble silver complexes and photosensitive reducible silver ion-containing compositions according to the present invention can be used to provide "precursor" articles that can then be used in various operations to provide electrically-conductive silver metal-containing thin film layers or electrically-conductive silver metal-containing thin film patterns for various uses in "product articles" as described below.

The term "precursor article" refers to an article (or element) designed to have a substrate having thereon a photosensitive thin film or photosensitive thin film pattern comprising a photosensitive reducible silver ion-containing composition as noted above as well as one or more photosensitizers and thus, are article in which silver reduction has not occurred to any appreciable extent.

The term "product article" then refers to an article (or element) in which silver ion reduction has occurred to at least some extent and hopefully to a significant extent during chosen operations as described below. Such product articles comprise a substrate having thereon a silver metal-containing thin film or silver metal-containing thin film pattern.

Both precursor articles and product articles have at least one feature in common, that is a suitable substrate that generally has two planar surfaces: a first supporting side (or surface) and a second opposing supporting side (or surface). Such substrates can have any suitable form such as sheets of any desirable size and shape, elongated fibers or woven fibers (such as in textiles) or other porous materials, polymeric beads of regular or irregular surface configuration (such as a curved or non-planar surface), and especially continuous webs of various materials that can be supplied, used, or stored as rolls.

More specifically, a uniform photosensitive thin film or one or more photosensitive thin film patterns are provided in a suitable manner on one or more supporting (planar) sides of a suitable substrate to provide a precursor article according to the present invention. Typically, photosensitive thin films or photosensitive thin film patterns are initially "wet" during and immediately after application to the substrate but the solvent medium can be removed as described below to provide the desired photosensitive thin films or photosensitive thin film pattern(s).

The photosensitive reducible silver ion-containing compositions according to this invention can be applied in a uniform or pattern-wise manner to any suitable substrate using any means for application, such as dip coating, roll coating, hopper coating, screen printing, spray coating, spin coating, inkjet printing, photolithographic imprinting, flexographic printing using printing elements including flexographic printing members (such as flexographic printing plates and flexographic printing sleeves), lithographic printing using lithographic printing plates, and gravure or intaglio printing using appropriate printing members. Inkjet printing and flexographic printing are particularly useful for providing photosensitive thin film patterns on one or both supporting sides of the substrate.

Suitable substrates (also known as "receiver elements") can be composed of any suitable material as long as it does not inhibit the purpose of the present invention to form silver metal within a uniform thin film or thin film pattern. For example, substrates can be formed from materials including but are not limited to, polymeric films, metals, glasses (untreated or treated for example with tetrafluorocarbon plasma, hydrophobic fluorine, or a siloxane water-repellant material), silicon or ceramic materials such as ceramic wafers, fabrics, papers, and combinations thereof (such as laminates of various films, or laminates of papers and films) provided that a uniform thin film or thin film pattern can be formed thereon in a suitable manner and followed by irradiation on at least one supporting side thereof. The substrate can be transparent or opaque, and rigid or flexible. The substrate can include one or more auxiliary polymeric or non-polymeric layers or one or more patterns of other materials before the photosensitive reducible silver ion-containing composition is applied according to the present invention.

Suitable substrate materials for forming precursor and product articles according to the present invention include but are not limited to, metallic films or foils, metallic films on polymer, glass, or ceramic materials, metallic films on electrically conductive film supports, semi-conducting organic or inorganic films, organic or inorganic dielectric films, or laminates of two or more layers of such materials. For example, useful substrates can include polymeric films such as poly(ethylene terephthalate) films, poly(ethylene naphthalate) films, polyimide films, polycarbonate films, polyacrylate films, polystyrene films, polyolefin films, and polyamide films, silicon and other ceramic materials, metal foils such as aluminum foils, cellulosic papers or resin-coated or glass-coated papers, glass or glass-containing composites, metals such as aluminum, tin, and copper, and metalized films. Porous fabrics, glasses, and polymeric webs can also be used.

Particularly useful substrates are polyesters films such as films of poly(ethylene terephthalate), polycarbonate, or poly(vinylidene chloride) films with or without surface-treatments or coatings as noted below, including continuous flexible webs of such polymers.

Either or both supporting sides (or surfaces) of the substrate can be treated for example with a primer layer or electrical or mechanical treatments (such as graining) to render that surface "receptive" to improve adhesion of the photosensitive reducible silver ion-containing composition and resulting photocured silver-containing thin film or photocured silver-containing thin film pattern. An adhesive layer can be disposed on the substrate and this adhesive layer can have various properties in response to stimuli (for example, it can be thermally activated, solvent activated, or chemically activated) and that serves to provide a receptive layer. Useful adhesive materials of this type are described for example in [0057] of U.S. Patent Application 2008/0233280 (Blanchet et al.).

In some embodiments, the substrate comprises a separate receptive layer as a receptive surface disposed on the supporting side of the substrate, which receptive layer and substrate can be composed of a material such as a suitable polymeric material that is highly receptive of the photosensitive reducible silver ion-containing composition. Such a receptive layer can have any suitable dry thickness of at least 0.05 μm when measured at 25° C.

The two (planar) supporting sides of the substrate, especially polymeric substrates, can be treated by exposure to corona discharge, mechanical abrasion, flame treatments, or oxygen plasmas, or by coating with various polymeric films, such as poly(vinylidene chloride) or an aromatic polysiloxane as described for example in U.S. Pat. No. 5,492,730 (Balaba et al.) and U.S. Pat. No. 5,527,562 (Balaba et al.) and U.S. Patent Application Publication 2009/0076217 (Gommans et al.).

Useful substrates can have a desired dry thickness depending upon the eventual use of the precursor article formed therefrom, for example its incorporation into various products articles or optical or display devices. For example, the substrate dry thickness (including all treatments and auxiliary layers) can be at least 0.001 mm and up to and including 10 mm, and especially for polymeric films, the substrate dry thickness can be at least 0.008 mm and up to and including 0.2 mm.

The substrate used to prepare the precursor and product articles described herein can be provided in various forms, such as for example, individual sheets in any size or shape, and continuous webs such as continuous webs of transparent substrates including transparent polyester substrates that are suitable for roll-to-roll operations. Such continuous webs can be divided or formed into individual first, second, and additional portions on first and second opposing supporting sides that can be used to form the same or different photosensitive thin film patterns in different portions of a supporting side (such as the first supporting sides) as well as same or different photoreduced silver-containing thin film patterns from the same or different photosensitive reducible silver ion-containing compositions.

In general, in the precursor article according to the present invention, the one or more non-hydroxylic-solvent soluble silver complexes can be present in the photosensitive thin film or the one or more photosensitive thin film patterns in a total amount of at least 95 weight % and up to and including 99 weight % based on the total dry weight of the photosensitive thin film or the one or more photosensitive thin film patterns. Moreover, one or more photosensitizers can be present in a total amount of at least 0.1 weight % and up to and including 4 weight %, or at least 1 weight % and up to and including 3 weight %, all photosensitizer amounts being based on the total amount of the total non-hydroxylic-solvent soluble silver complexes.

In some embodiments, a precursor article can further comprise one or more photosensitive thin film patterns on the second opposing supporting side of the substrate, each of the one or more photosensitive thin film patterns disposed on the second opposing supporting side, comprising:

a) one or more non-hydroxylic-solvent soluble silver complexes as described above; and b) one or more photosensitizers as described above.

Product Articles

The product articles provided by the methods according to the present invention described below generally have the same structure and components as the precursor articles except that most or all of the reducible silver ions have been reduced to electrically-conductive silver metal in the corresponding electrically-conductive thin films or electrically-conductive thin film patterns. In some embodiments, the product articles can be provided in any suitable form such as individual sheets of any suitable size and shape, films or webs whose ends are attached to each other, wound rolls of continuous material with or without a core material, spindle, or mandrel.

In other embodiments, where inventive complexes, photosensitive compositions, and methods can be used to generate electrically-conductive metallic silver patterns and electrodes within various devices, including but not limited to, membrane touch switch (MTS), battery testers, biomedical, electroluminescent lamps, radio frequency identification (RFID) antenna, flat panel displays such as plasma display panel (PDP) and organic light emitting diode (OLED) display, printed transistors and circuits, thin film photovoltaics, and other devices that would be readily apparent to one skilled in the art. In other words, such "product" articles according to this invention are device themselves rather than articles that are incorporated into a device. Alternatively, the product articles are devices themselves that also have another product article incorporated therein.

Electrically-conductive thin film patterns can be created according to the present invention using photolithography to create high-fidelity features. Both positive and negative patterning processes may be used to create such patterns.

Such product articles comprise a substrate having a first supporting side and a second opposing supporting side. On at least the first supporting side, are:

an electrically-conductive silver metal-containing thin film or one or more electrically-conductive silver metal-containing thin film patterns, comprising:

silver metal;

an α-oxy carboxylate (residual amounts of the L component from formula (1)) as described above;

a primary alkylamine (residual amounts of the P component from formula (1)); and one or more photosensitizers as described above that can either reduce reducible silver ion or oxidize the α-oxy carboxylate.

Depending upon how the precursor article is designed, the product article can comprise two or more electrically-conductive silver metal-containing thin film patterns in different portions on the first supporting side of the substrate.

In addition, a product article can further comprise one or more electrically-conductive silver metal-containing thin film patterns in different portions on the second opposing supporting side of the substrate, each of these one or more electrically-conductive silver metal-containing thin film patterns comprising:

silver metal;

an α-oxy carboxylate (that is, residual amounts of the L component of formula (1) as described above);

a primary alkylamine (that is, residual amounts of the P component of formula (1) described above); and one or more photosensitizers as described above that can either reduce reducible silver ion or oxidize the α-oxy carboxylate.

For example, in such embodiments, the product articles can comprise:

silver metal;

residual α-oxy carboxylate having a molecular weight of 150 or less, and that is represented by either the following formula (II) or (III):

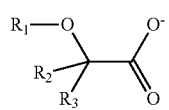

(II)

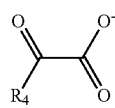

(III)

wherein $R_1$ is hydrogen or a branched or linear alkyl group having 1 to 3 carbon atoms, $R_2$ and $R_3$ are independently branched or linear alkyl groups having 1 to 8 carbon atoms, wherein any of the hydrogen atoms in the $R_1$, $R_2$, and $R_3$ branched or linear alkyl groups optionally can be replaced with a fluorine atom, and $R_4$ is a branched or linear alkyl group having 1 to 8 carbon atoms wherein any of the hydrogen atoms optionally can be replaced with a fluorine atom; and residual primary alkylamine that is selected from the group consisting of a propylamine, an n-butylamine, a t-butylamine, isopropylamine, 2,2,2-trifluoroethylamine, 2,2,3,3,3-pentafluoropropylamine, 3,3,3-trifluoropropylamine, 1,2-dimethylpropylamine, t-amyl amine, isopentylamine, 2-amino-3-methylbutane, 3,3-dimethyl-2-butylamine, 2-aminohexane, and sec-butylamine.

Method for Providing Silver Metal

The precursor articles are prepared and used according to the present invention by firstly providing a suitable photosensitive thin film on a substrate as described above. This can be accomplished in a number of ways.

In some embodiments, a photosensitive reducible silver ion-containing composition according to the present invention can be disposed in a uniform manner onto one or both supporting sides of the substrate (with or without adhesion treatments), such as a polymeric film (for example, as a continuous polyester web), glass, paper, cardboard, or ceramic material A variety of films, including for example polymer films composed of polyethylene, polypropylene, biaxially oriented polypropylene, polyethylene terephthalate, polybutylene terephthalate and polyamide, can be utilized as suitable substrates. The choice of substrate structure is not, however, limited to films but includes polymers or copolymers or polymer blends formed into bags, shrink wrap, plates, cartons, boxes, bottles, crates, and other containers. Similarly, the range of suitable substrate compositions is not limited to polymers and copolymers, but can include papers such as pre-coated papers, cardboard such as pre-coated cardboard, and other common packaging materials. Such composition application can be carried out for example, uniform inkjet printing or using a blade coating, gap coating, slot die coating, X-slide hopper coating, or knife on roll operation.

After application of the photosensitive reducible silver ion-containing composition in this manner, if desired, at least 50 weight % and up to and including 100 weight % of the original solvent medium (and any water) can be removed in any suitable manner. For example, ambient drying can be carried out in an open environment, of the resulting precursor article can be subject to an "active" drying operation and apparatus that do not adversely affect the non-hydroxylic-solvent soluble silver complex (and photosensitizer if present) in the precursor article, or prematurely cause reduction of the silver ions. Useful drying conditions can be as low as room temperature for as little as 5 seconds and up to and including several hours depending upon the manufacturing process. In many processes, such as roll-to-roll processes in manufacturing operations, drying conditions can be employed at any suitable temperature, for example greater than 50° C. to remove at least 90 weight % (and up to 100 weight %) of the original solvent medium (and any water) within at least 10 seconds or within 5 seconds or within 1 second.

The one or more non-hydroxylic-solvent soluble silver complexes can be present in the photosensitive thin film or photosensitive thin film pattern in an amount of at least 96 weight % and up to and including 99.5 weight % based on the total weight of the photosensitive thin film or photosensitive thin film pattern; and the photosensitizer is present in an amount of at least 0.5 weight % and up to and including 4 weight %, based on the total weight of the one or more non-hydroxylic-solvent soluble silver complexes.

The resulting photosensitive thin films generally have a dry average thickness of at least 100 nm and up to and including 1,500 nm, or more likely at least 500 nm and up to and including 1000 nm ("average" determined by two or more measurements in different locations). The dry thickness can vary to some degree throughout the photosensitive thin film. The term "uniform" in this context does not necessary mean that the dry thickness must always be the same, but that the entire surface of the supporting side of the substrate is completely covered.

Alternative to depositing the photosensitive reducible silver ion-containing composition in a uniform manner, it can be applied to the substrate (one or both supporting sides) in a patternwise fashion using techniques described below such as flexographic printing or inkjet printing to provide one or more photosensitive thin film patterns.

Any applied photosensitive thin film pattern can comprise a grid of lines (or other shapes including circles or an irregular network), each having a dry average thickness (or width) of at least 1000 nm and up to and including 10 mm, or typically of at least 5 μm and up to and including 1 mm, and the optimal dry thickness (or width) can be tailored for an intended use.

In some embodiments, the same or different photosensitive reducible silver ion-containing composition can be applied in a suitable manner in different portions on both the first supporting side and the second opposing supporting side of the substrate to form "duplex" or dual-sided precursor articles, and each applied photosensitive reducible silver ion-containing composition can be in the form of the same or different photosensitive thin film pattern.

In many embodiments, a photosensitive reducible silver ion-containing composition is applied on one or both supporting sides of the substrate (for example as a roll-to-roll web) using a relief element such as elastomeric relief elements derived from flexographic printing plate precursors, many of which are known in the art and some are commercially available, for example as the CYREL®

Flexographic Photopolymer Plates from DuPont and the Flexcel SR and NX Flexographic plates from Eastman Kodak Company.

Particularly useful elastomeric relief elements are derived from flexographic printing plate precursors and flexographic printing sleeve precursors, each of which can be appropriately imaged (and processed if needed) to provide the relief elements for "printing" suitable photosensitive thin film patterns as described for example, in U.S. Pat. No. 7,799,504 (Zwadlo et al.) and U.S. Pat. No. 8,142,987 (Ali et al.) and U.S. Patent Application Publication 2012/0237871 (Zwadlo), the disclosures of all of which are incorporated herein by reference for details of such flexographic printing member precursors. Such elastomeric photopolymerizable layers can be imaged through a suitable mask image to provide an elastomeric relief element (for example, flexographic printing plate or flexographic printing sleeve). The relief layer can be different if different patterns of photosensitive reducible silver ion-containing compositions are applied to opposing supporting sides of the substrate.

In other embodiments, the elastomeric relief element is provided from a direct (or ablation) laser-engraveable elastomer relief element precursor, with or without integral masks, as described for example in U.S. Pat. No. 5,719,009 (Fan), U.S. Pat. No. 5,798,202 (Cushner et al.), U.S. Pat. No. 5,804,353 (Cushner et al.), U.S. Pat. No. 6,090,529 (Gelbart), U.S. Pat. No. 6,159,659 (Gelbart), U.S. Pat. No. 6,511,784 (Hiller et al.), U.S. Pat. No. 7,811,744 (Figov), U.S. Pat. No. 7,947,426 (Figov t al.), U.S. Pat. No. 8,114,572 (Landry-Coltrain at al.), U.S. Pat. No. 8,153,347 (Veres et al.), U.S. Pat. No. 8,187,793 (Regan et al.), and U.S. Patent Application Publications 2002/0136969 (Hiller t al.), 2003/0129530 (Leinenbeck at al.), 2003/0136285 (Telser at al.), 2003/0180636 (Kanga et al.), and 2012/0240802 (Landry-Coltrain et al.), the disclosures of all of which are incorporated herein for details of such laser-engraveable precursors.

When the noted elastomeric relief elements are used in the present invention, the photosensitive reducible silver ion-containing composition can be applied in a suitable manner to the uppermost relief surface (raised surface) in the elastomeric relief element. Application to a substrate can be accomplished in a suitable procedure and it is desirable that as little as possible is coated onto the sides (slopes) or recesses of the relief depressions. Anilox roller systems or other roller application systems, especially low volume Anilox rollers, below 2.5 billion cubic micrometers per square inch (6.35 billion cubic micrometers per square centimeter) and associated skive knives can be used.

In such embodiments, the photosensitive reducible silver ion-containing composition can have a viscosity during this application of at least 1 cps (centipoise) and up to and including 5000 cps, or at least 1 cps to and up to and including 1500 cps. The photosensitive reducible silver ion-containing composition can be fed from an Anilox or other roller inking system in a measured amount for each printed precursor article. In one embodiment, a first roller can be used to transfer the photosensitive reducible silver ion-containing composition from an "ink" pan or a metering system to a meter roller or Anilox roller. Such composition is generally metered to a uniform thickness when it is transferred from the Anilox roller to a printing plate cylinder. When the substrate is moved through the roll-to-roll handling system from the printing plate cylinder to an impression cylinder, the impression cylinder applies pressure to the printing plate cylinder that transfers an image from an elastomeric relief element to the substrate in forming a precursor article.

Once the photosensitive thin films or photosensitive thin film patterns are provided, such precursor articles can be then appropriately exposed (for example using radiation having a wavelength of at least 150 nm and up to and including 700 nm) to photochemically convert the reducible silver ions to silver metal, for example in the presence of oxygen, to provide product articles comprising silver metal-containing thin films or one or more silver metal-containing thin film patterns. This exposing operation can be carried out at room temperature or more likely under either ambient or controlled conditions at a temperature of at least 45° C. It would be apparent that such temperature conditions can vary with the specific exposing devices that are used.

For example, irradiation can be carried out using a suitable source such as a fluorescent lamp or LED to provide a silver metal-containing thin film or silver metal-containing thin film pattern. For example, silver ion reduction can be achieved by the use of UV or visible irradiation having a wavelength of at least 150 nm and up to and including 700 nm and at intensity of at least 1,000 microwatts/cm$^2$ and up to and including 80,000 microwatts/cm$^2$. The irradiation system used to generate such radiation can consist of one or more ultraviolet lamps for example in the form of 1 to 50 discharge lamps, for example, xenon, metallic halide, metallic arc (such as a low, medium or high pressure mercury vapor discharge lamps having the desired operating pressure from a few millimeters to about 10 atmospheres). The lamps can include envelopes capable of transmitting light of a wavelength of at least 150 nm and up to and including 700 nm or typically at least 240 nm and up to and including 450 nm. The lamp envelope can consist of quartz, such as Spectrocil or Pyrex. Typical lamps that can be employed for providing ultraviolet radiation are, for example, medium pressure mercury arcs, such as the GE H3T7 arc, a Hanovia 450 W arc lamp, and Fusion F300S, F600S, and F300SQ microwave-powered electrodeless lamps. Silver ion photochemical reduction can be carried out using a combination of various lamps, some of or all of which can operate in an inert atmosphere. When using UV lamps, the irradiation flux impinging upon the substrate (or applied layer or pattern) can be at least 0.01 watts/inch$^2$ (0.0197 watts/cm$^2$) to effect sufficient rapid silver ion photoreduction within 1 to 20 seconds in a continuous manner, for example in a roll-to-roll operation. In some embodiments, a pulsed light source can be used to cause the photochemical reaction. The duration and rate of pulse can be varied to achieve the desired light dosage within the desired irradiation time.

An LED irradiation device to be used in the photochemical reduction can have an emission peak wavelength of 350 nm or more. The LED device can include two or more types of elements having different emission peak wavelengths greater than or equal to 350 nm. A commercial example of an LED device that has an emission peak wavelength of 350 nm or more and has an ultraviolet light-emitting diode (UV-LED) is NCCU-033 that is available from Nichia Corporation.

Each precursor article can be irradiated individually as a single element, or in alternative embodiments, as a web (for example, a roll-to-roll continuous web) containing multiple precursor articles in multiple portions of the continuous web that is passed through exposure stations, or the exposure device is passed over the continuous web. The same or different photosensitive reducible silver ion-containing compositions can be applied (for example, printed) on both supporting sides of the substrate whether it is in the form of a single element or continuous web. In many embodiments, different photosensitive thin film patterns can be formed on opposing supporting sides of the substrate (or continuous web).

The result of such irradiation of a precursor article is a product article as described above comprising the substrate (for example, individual sheets or a continuous web) and having thereon either an electrically-conductive silver metal-containing thin film or one or more electrically-conductive silver metal-containing thin film patterns on one or both supporting sides of the substrate.

In general, the electrically-conductive silver metal-containing thin film or electrically-conductive silver-containing thin film patterns has a resistivity of less than $10^6$ ohms/□ as measured using a 4-point probe device. In particular embodiments, each electrically-conductive silver-containing thin film or electrically-conductive silver-containing thin film pattern has a resistivity of less than 1000 ohms/□, or a resistivity of less than 500 ohm/□, or even less than 100 ohms/□.

After irradiation, the product articles can be contacted (washed) with water for up to 5 minutes at a temperature of at least 20° C. and up to and including 90° C. Such water contacting can be used to remove impurities as well as to enhance electrical conductivity of the electrically-conductive silver metal-containing thin film or one or more electrically-conductive silver metal-containing thin film patterns. Residual water can be removed after this step using any suitable drying operation, for example as described above for other drying operations.

In some embodiments, a method according to the present invention for providing two or more electrically-conductive patterns on a continuous substrate having a first supporting side and a second opposing supporting side, comprises:
providing a continuous substrate,
providing two or more photosensitive thin film patterns on two or more respective portions on the first supporting side of the continuous substrate, each of the two or more photosensitive thin film patterns comprising:
   a) a non-hydroxylic-solvent soluble silver complex comprising: a reducible silver ion complexed with an α-oxy carboxylate and a primary alkylamine,
   the non-hydroxylic-solvent soluble silver complex being represented by the following formula (I):

$(Ag^+)_a(L)_b(P)_c$              (I)

wherein L represents the α-oxy carboxylate; P represents the primary alkylamine; a is 1 or 2; b is 1 or 2; and c is 1, 2, 3, or 4, provided that when a is 1, b is 1, and when a is 2, b is 2; and
   b) a photosensitizer that can either reduce the reducible silver ion or oxidize the α-oxy carboxylate;
photochemically converting reducible silver ions in each of the two or more photosensitive thin film patterns on the first supporting side of the continuous substrate to provide correspondingly two or more electrically-conductive silver metal-containing patterns;
contacting each of the two or more electrically-conductive silver metal-containing patterns with water or an aqueous or non-aqueous salt solution (as described below);
optionally, contacting each of the two or more electrically-conductive silver metal-containing patterns with an aqueous or non-aqueous non-salt solution (as described below); and
optionally, drying each of the two or more electrically-conductive silver metal-containing patterns on the supporting side of the continuous substrate. Such drying can be carried out using any suitable drying conditions and equipment, for example as described above for other drying operations.

Such a method can further comprise:
providing two or more opposing photosensitive thin film patterns on two or more respective portions on the second opposing supporting side of the continuous substrate, each of the two or more opposing photosensitive thin film patterns comprising:
   a) the non-hydroxylic-solvent soluble silver complex; and
   b) the photosensitizer;
photochemically converting reducible silver ions in each of the two or more opposing photosensitive thin film patterns to provide two or more opposing electrically-conductive silver metal-containing patterns on the second opposing supporting side of the continuous substrate;
contacting each of the two or more opposing electrically-conductive silver metal-containing patterns with water or an aqueous or non-aqueous salt solution (as described below);
optionally, contacting each of the two or more opposing electrically-conductive silver metal-containing patterns with an aqueous or non-aqueous non-salt solution (as described below); and
optionally, drying each of the two or more opposing electrically-conductive silver metal-containing patterns. Such drying can be carried out using any suitable drying conditions and equipment, for example as described above for other drying operations.

When such a method is carried out, all of the photosensitive thin film patterns on both the first supporting side and the second opposing supporting side of the continuous substrate, can be provided using the same or different flexographic printing members.

Silver Conductivity Enhancement:

Once electrically-conductive metallic silver has been generated in a product article as described above, its electrical conductivity can be enhanced in some embodiments using one or more (or even two or more) treatment cycles comprising contact of the product article with an aqueous or non-aqueous salt solution containing a salt (as described below) followed by drying the product article. Thus, such treatment cycles are optional but when they are used, each of these two-step treatment cycle comprises two essential features: (1) contacting the silver metal in the product article with the aqueous or non-aqueous salt solution, and (2) optionally, drying the electrically-conductive silver metal in the product article (for example, as described above for other drying operations). It is particularly useful for the method according to this invention to comprise two or more additional two-step treatment cycles beyond the first two-step treatment cycle, with drying after each contacting step in each two-step treatment cycle, to enhance the electrical conductivity of the silver metal in the product article provided according to this invention. The result of these processes is the provision of "treated silver metal" in the product article.

Each two-step treatment cycle can be carried out using the same or different aqueous or non-aqueous salt solution. Thus, the same or different salts can be used in the multiple two-step treatment cycles, but in most embodiments where multiple two-step treatment cycles are used, the same salt is used in each two-step treatment cycle. Useful salts are described below.

As used herein for the treatment cycles, the term "aqueous" means that the solution (whether salt solution or non-salt solution) comprises water as the predominant solvent among the total solvents in the solution. That means that greater than 60 volume % of the total volume of solvents is composed of water. Generally, such aqueous solutions comprise water in an amount of at least 90 volume % of total solvents.

As used herein for the treatment cycles, the term "non-aqueous" means that the solution (whether salt solution or non-salt solution) comprises one or more organic solvents (described below) as the predominant solvent(s) among the total solvents in the solution. That means that greater than 60 volume % of the total volume of solvents is composed of one or more organic solvents. Generally, such non-aqueous solutions comprise one or more organic solvents in an amount of at least 90 volume % of total solvents.

Each treatment cycle can further include an additional contacting step whereby the electrically-conductive silver metal is contacted with an aqueous or non-aqueous non-salt solution (that does not contain any salts described for the aqueous or non-aqueous salt solutions) after contacting the product article with the aqueous or non-aqueous salt solution but before drying the product article. Such aqueous or non-aqueous non-salt solutions can be composed predominantly of water. Alternatively, the non-salt solutions can be comprised of predominantly one or more organic solvents as described below and thus be non-aqueous non-salt solutions.

The use of a non-salt aqueous or non-aqueous solution contacting step is not essential, but it can be very desirable in many embodiments. Thus, such a three-step treatment cycle would include (1) contacting the product article with an aqueous or non-aqueous salt solution, (1a) contacting the product article with an aqueous or non-aqueous non-salt solution (such as plain water), and (2) optionally, drying the product article (using conditions described above). Each of these three-step treatment cycles can be used multiple times, or only one time along with one or more of the two-step treatment cycles described above.

In each two-step or three-step treatment cycle, the product article can be contacted with an aqueous or non-aqueous salt solution in any suitable manner, such as by spraying, coating, immersion into a bath, or another contacting means that would be readily apparent to one skilled in the art. The aqueous or non-aqueous salt solution is generally used at a temperature of at least 20° C. or at least 30° C. and up to and including 90° C., or at least 45° C. and up to and including 80° C., or even at least 40° C. and up to and including 70° C. The temperature can be the same or different for each of the treatment cycles. The temperature can be adjusted for a given type of aqueous or non-aqueous solution and depending upon whether a salt is present or not.

Contacting with an aqueous or non-aqueous non-salt solution in a three-step treatment cycle can be carried out within the same temperature ranges using the same or different contacting means, but the temperature need not be the same as that used for the aqueous or non-aqueous salt solution in each three-step treatment cycle.

For each two-step or three-step treatment cycle, the noted contacting with an aqueous or non-aqueous salt solution can be generally carried out for at least 6 seconds and up to and including 30 minutes or more likely for at least 30 seconds and up to and including 20 minutes, but a particularly useful time for this contacting in at least one two-step treatment cycle is at least 15 seconds and up to and including 1 minute so that each two-step or three-step treatment cycle is relatively short. The contacting times for the multiple two-step or three-step treatment cycles can be the same or different. However, in some embodiments, the contacting time in the first two-step or three-step treatment cycle can be longer than the contacting time in the successive two-step or three-step treatment cycle(s).

The contacting steps in the three-step treatment cycles using the aqueous or non-aqueous non-salt solutions can be similarly carried out using the times, temperatures, and contacting means described above for contacting with the aqueous or non-aqueous salt solutions, but the times, temperatures, and contacting means need not be the same for each type of contacting, or for each two-step or three-step treatment cycle.

The drying operation for each two-step or three-step treatment cycle, when used, can be carried out using any suitable drying means, such as ambient (unassisted) drying means, or active use of hot air or unassisted evaporation, and the drying time and temperature can be readily determined with routine experimentation (other conditions described above). The drying means can be the same or different for each two-step or three-step treatment cycle.

Useful salts for the aqueous salt solutions used in the same or different two-step or three-step treatment cycles include but are not limited to, one or more chloride salts (such as sodium chloride, potassium chloride, and ammonium chloride), bromide salts (such as sodium bromide, potassium bromide, and ammonium bromide), silver salts (such as silver nitrate, silver acetate, and others known in the art). The salts can be used singly or in combination, and their total concentration in the aqueous salt solution is generally at least 0.1 weight % and up to and including 20 weight %, or typically at least 1 weight % and up to and including 10 weight %. Particularly useful salts are the chloride salts, singly or in combination.

Useful salts for the non-aqueous salt solutions for the same or different treatment cycles include but are not limited to, one or more chloride salts (such as tetrabutylammonium chloride), bromide salts (such as tetrabutylammonium bromide), silver salts (such as silver nitrate). The salt can be used singly or in combination, and their total concentration in the solvent salt solution is generally at least 0.1 weight % and up to and including 20 weight %, or typically at least 1 weight % and up to and including 10 weight %. Particularly useful salts are the chloride salts, singly or in combination Each aqueous salt solution or aqueous non-salt solution generally has a pH of at least 4 and up to and including 11, or typically a pH of at least 6 and up to and including 8. The pH can be adjusted using a suitable alkaline compound (such as a hydroxide) and any suitable buffer can be included to maintain the desired pH, as long as these additional components do not detract from the desired effect of enhancing electrical conductivity of the silver metal in the product articles. The non-salt aqueous solutions can be plain water with nothing added, but they can optionally include a surfactant, biocide, or buffer if desired.

Non-aqueous salt solutions and aqueous non-salt solutions contain one or more organic solvents that include, but are not limited to, acetonitrile, butyronitrile, propionitrile, acetone, 2-butanone, methanol, ethanol, iso-propanol, and other similar organic solvents that would be readily apparent to one skilled in the art.

Thus, in some embodiments of the present invention, after a product article is provided using the photochemical reduction of reducible silver ions describe above, the product article can be subjected to two or more two-step or three-step treatment cycles wherein each two-step or three-step treatment cycle includes essential steps (1) and (2) described above, but each three-step treatment cycle includes step (1a) described above. Each contacting step (1) can be carried out for at least 1 second and up to and including 60 seconds at a temperature noted above, with one or more salts having a total salt concentration of at least 0.01 mol/l and up to and including 0.5 mol/l, and contacting step (1a) can be carried out for a similar time particularly using plain water.

In some embodiments, after a product article is provided using the photochemical reduction of reducible silver ions describe above, the product article containing silver metal can be sprayed with water, or an aqueous or non-aqueous salt solution followed by suitable drying.

In other embodiments once the metallic silver is formed, the product article can be contacted with (1) a non-aqueous salt-containing solution, and (2) optional drying. It is particularly desired to use two or more additional two-step treatment cycles beyond this first two-step treatment cycle to enhance the electrical conductivity of the silver metal in the product article.

Moreover, as described above, each two-step treatment cycle can be converted into a three-step treatment cycle to include (1a) contacting the silver metal with an aqueous or non-aqueous non-salt aqueous solution before any drying.

Thus, after photochemically converting the reducible silver ions to silver metal, the method can include contacting the electrically-conductive silver metal-containing thin film or electrically-conductive silver metal-containing thin film pattern with water or an aqueous or non-aqueous salt solution, and optionally, drying the silver metal-containing thin film or silver metal-containing thin film pattern.

Alternatively, the method according to this invention, comprises:

after photochemically converting the reducible silver ions to silver metal, contacting the electrically-conductive silver metal-containing thin film or electrically-conductive silver metal-containing thin film pattern with water or an aqueous or non-aqueous non-salt solution, and optionally, drying the electrically-conductive silver metal-containing thin film or electrically-conductive silver metal-containing thin film pattern.

In other embodiments, the method according to the present invention, comprises:

after photochemically converting the reducible silver ions to silver metal, contacting the electrically-conductive silver metal-containing thin film or electrically-conductive silver metal-containing thin film pattern with an aqueous or non-aqueous salt solution, contacting the electrically-conductive silver metal-containing thin film or electrically-conductive silver metal-containing thin film pattern with water of an aqueous or non-aqueous non-salt solution, and optionally, drying the electrically-conductive silver metal-containing thin film or electrically-conductive silver metal-containing thin film pattern.

The present invention provides at least the following embodiments and combinations thereof, but other combinations of features are considered to be within the present invention as a skilled artisan would appreciate from the teaching of this disclosure:

1. A non-hydroxylic-solvent soluble silver complex comprising: a reducible silver ion complexed with an α-oxy carboxylate and a primary alkylamine, the non-hydroxylic-solvent soluble silver complex being represented by the following formula (I):

$$(Ag^+)_a(L)_b(P)_c \quad (I)$$

wherein L represents the α-oxy carboxylate; P represents the primary alkylamine; a is 1 or 2; b is 1 or 2; and c is 1, 2, 3, or 4, provided that when a is 1, b is 1, and when a is 2, b is 2.

2. The non-hydroxylic-solvent soluble silver complex of embodiment 1, wherein L is represented by the following formula (II):

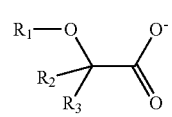

(II)

wherein $R_1$, $R_2$, and $R_3$ are independently hydrogen or linear or branched alkyl groups.

3. The non-hydroxylic-solvent soluble silver complex of embodiment 2, wherein $R_1$ is hydrogen or a branched or linear alkyl group having 1 to 3 carbon atoms, and $R_2$ and $R_3$ are independently branched or linear alkyl groups having 1 to 8 carbon atoms, wherein any of the hydrogen atoms in the $R_1$, $R_2$, and $R_3$ branched or linear alkyl groups optionally can be replaced with a fluorine atom.

4. The non-hydroxylic-solvent soluble silver complex of any of embodiments 1 to 3, wherein the α-oxy carboxylate has a molecular weight of 250 or less.

5. The non-hydroxylic-solvent soluble silver complex of embodiment 1 or 4, wherein L is represented by the following formula (III):

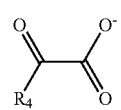

(III)

wherein $R_4$ is a branched or linear alkyl group having 1 to 8 carbon atoms and any of the hydrogen atoms in the $R_4$ branched or linear alkyl group optionally can be substituted with a fluorine atom.

6. The non-hydroxylic-solvent soluble silver complex of any of embodiments 1 to 5, wherein the α-oxy carboxylate is selected from the group consisting of lactate, 2-hydroxybutyric acid, 2-hydroxy-3-methylbutyric acid, 2-hydroxy-3,3-dimethylbutyric acid, 2-hydroxy-isobutyric acid, 2-hydroxy-2-methylbutyric acid, 2-ethyl-2-hydroxybutyric acid, 2-hydroxy-2,3-dimethylbutyric acid, 2-ethyl-2-methoxybutyric acid, 2-methoxy-2-methylpropanoic acid, 1-hydroxycyclopentane-1-carboxylic acid, 2,3-dihydroxy-2,3-dimethylsuccinic acid, and 2,4-dihydroxy-2,4-dimethylpentanedioic acid, or selected from the group consisting of pyruvic acid, 3-methylpyruvic acid, 3,3-dimethylpyruvic acid, 3,3-dimethyl-2-oxobutanoic acid, 3,3-dimethyl-2-oxopentanoic acid, and 2,3-dioxosuccinic acid.

7. The non-hydroxylic-solvent soluble silver complex of any of embodiments 1 to 6, wherein P is a primary alkylamine having a boiling point of less than or equal to 175° C.

8. The non-hydroxylic-solvent soluble silver complex of any of embodiments 1 to 7, wherein P is a primary alkylamine having a boiling point of less than or equal to 125° C.

9. The non-hydroxylic-solvent soluble silver complex of any of embodiments 1 to 8, wherein the primary alkylamine has an oxidation potential of greater than 1.0 V vs. SCE; the α-oxy carboxylate has a first oxidation potential of at least 1.2 V vs. SCE; and upon decarboxylation of the α-oxy carboxylate, a second radical is generated that has an oxidation potential of less than 1.0 V vs. SCE.

10. The non-hydroxylic-solvent soluble silver complex of any of embodiments 1 to 9, wherein the primary alkylamine has an oxidation potential of greater than 1.4 V vs. SCE.

11. The non-hydroxylic-solvent soluble silver complex of any of embodiments 1 to 10, wherein the primary alkylamine has a pKa of at least 1 and up to and including 30 as measured in acetonitrile.

12. The non-hydroxylic-solvent soluble silver complex of any of embodiments 1 to 11, wherein the primary alkylamine has a pKa of at least 10 and up to and including 25 as measured in acetonitrile, and the primary alkylamine has an oxidation potential that is greater than 1.0 V vs. SCE.

13. The non-hydroxylic-solvent soluble silver complex of any of embodiments 1 to 12, wherein the primary alkylamine comprises a branched or linear alkyl group having 3 to 6 carbon atoms.

14. The non-hydroxylic-solvent soluble silver complex of any of embodiments 1 to 13, wherein the primary alkylamine is selected from the group consisting of propylamine, n-butylamine, t-butylamine, isopropylamine, 2,2,2-trifluoroethylamine, 2,2,3,3,3-pentafluoropropylamine, 3,3,3-trifluoropropylamine, 1,2-dimethylpropylamine, t-amyl amine, isopentylamine, 2-amino-3-methylbutane, 3,3-dimethyl-2-butylamine, 2-aminohexane, and sec-butylamine.

15. The non-hydroxylic-solvent soluble silver complex of any of embodiments 1 to 14, which meets a silver ion stability test such that when the non-hydroxylic-solvent soluble silver complex is held for 24 hours at ambient temperature and under yellow safelight, less than 0.1 mol % of its original silver ion content is reduced to silver metal.

16. The non-hydroxylic-solvent soluble silver complex of any of embodiments 1 to 15, wherein:

L has a molecular weight of 250 or less, and L is represented by either the following formula (II) or (I):

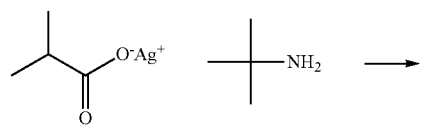

wherein $R_1$ is hydrogen or an alkyl group having 1 or 2 carbon atoms, $R_2$ and $R_3$ are independently branched or linear alkyl groups having 1 to 8 carbon atoms, wherein any of the hydrogen atoms in the $R_1$, $R_2$, and $R_3$ branched or linear alkyl groups optionally can be replaced with a fluorine atom, and $R_4$ is a branched or linear alkyl group having 1 to 8 carbon atoms wherein any of the hydrogen atoms optionally can be replaced with a fluorine atom; and P is a primary alkylamine that is selected from the group consisting of propylamine, n-butylamine, t-butylamine, isopropylamine, 2,2,2-trifluoroethylamine, 2,2,3,3,3-pentafluoropropylamine, 3,3,3-trifluoropropylamine, 1,2-dimethyl-propylamine, t-amyl amine, isopentylamine, 2-amino-3-methylbutane, 3,3-dimethyl-2-butylamine, 2-aminohexane, and sec-butylamine.

17. The non-hydroxylic-solvent soluble silver complex of any of embodiments 1 to 16, wherein:

(i) a and b are both 1 and c is 1 or 2;

(ii) a and b are both 2 and c is 2; or (iii) a and b are both 2 and c is 4.

The following Examples are provided to illustrate the practice of this invention and are not meant to be limiting in any manner.

Most reagents and solvents used in the following Examples can be obtained from various commercial sources such as VWR, Sigma-Aldrich Chemical Co. (Milwaukee, Wis., USA) and Fisher Scientific (Pittsburgh, Pa., USA).

Comparative Example 1: Preparation of Silver Isobutyrate t-Butylamine Complex

To a slurry of silver isobutyrate (1 g, 5.18 mmol) in acetonitrile (4 ml), t-butylamine (0.378 g, 5.18 mmol) was added and the resulting reaction mixture was stirred to obtain a clear solution. The clear reaction solution was stirred at 25° C. for 10 minutes and acetonitrile was slowly removed at room temperature to obtain a white solid of the desired silver isobutyrate t-butylamine complex that was characterized by $^1$H NMR (CD$_3$CN) δ 4.3 (q, 1H), 1.35 (d, 3H), 1.25 (s, 9H).

Attempted Photochemical Generation of Electrically-Conductive Silver Metal Using an Alkyl Carboxylate-Primary Amine Complex:

Silver isobutyrate t-butylamine complex described above (0.2 g) was dissolved in acetonitrile (1 ml). Photosensitizer PS-7 (0.02 g; 2 weight %) was added to the solution and dissolved at room temperature to form a photosensitive silver ion-containing composition. This composition was spin coated on a glass plate substrate at 800 rpm to form a thin form on the substrate. The resulting precursor article that was then exposed to UV light using a medium pressure Hg/Xe (1000 W) lamp. The color of the thin film changed from colorless to yellow in 20 seconds, indicating the formation of silver nanoparticles (UV/V is absorption spectrum shows an absorption in the 400-425 nm range typically associated with the presence of silver metal). Upon further irradiation, the color of the thin film slowly changed from yellow to brown indicating formation of larger size silver nanoparticles. The sheet resistivity of the resulting printed silver metal features was measured using a 4-point probe device and found to be non-electrically conductive. The thin film resistivity did not change after washing it with a brine (sodium chloride) solution (0.1 molar) for 10 seconds.

This example demonstrates that upon UV irradiation, a silver ion-containing composition comprising a complex of a silver alkyl carboxylate with an alkylamine, and a photosensitizer does not generate metallic silver.

Inventive Example 1: Preparation of Silver Lactate n-Propylamine Complex

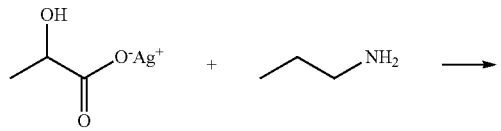

To a slurry of silver lactate (1.0 g, 5.076 mmol) in acetonitrile (4 ml), n-propyl amine (0.3 g, 5.08 mmol) was added to obtain a clear reaction solution. The reaction solution was stirred at 25° C. for 10 minutes and then the acetonitrile was slowly removed at room temperature to obtain a white solid of the desired silver lactate n-propylamine complex as confirmed by $^1$H NMR ($CD_3CN$).

Inventive Example 2: Preparation of Silver Lactate t-Butylamine Complex

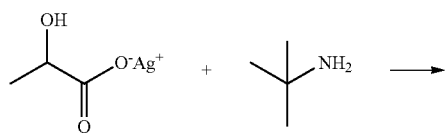

To a slurry of silver lactate (1.0 g, 5.076 mmol) in acetonitrile (4 ml), t-butylamine (0.37 g, 5.08 mmol) was added to obtain a clear reaction solution. The reaction solution was stirred at 25° C. for 10 minutes and then the acetonitrile was slowly removed at room temperature to obtain a white solid of the desired silver lactate t-butylamine complex as confirmed by $^1$H NMR ($CD_3CN$).

Inventive Example 3: Preparation of Silver 2-Hydroxyisobutyrate Tert-Amylamine Complex

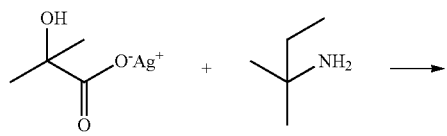

To a slurry of silver 2-hydroxybutyrate (1.0 g, 4.76 mmol) in acetonitrile (4 ml), t-amylamine (0.757 g, 8.63 mmol) was added to obtain a clear reaction solution. The reaction solution was stirred at 25° C. for 10 minutes and then the acetonitrile was slowly removed at room temperature to obtain a white solid of the desired silver 2-hydroxyisobutyrate t-amylamine complex as confirmed by $^1$H NMR ($CD_3CN$).

Inventive Example 4: Preparation of Silver 2-Hydroxyisobutyrate Tert-Butylamine Complex

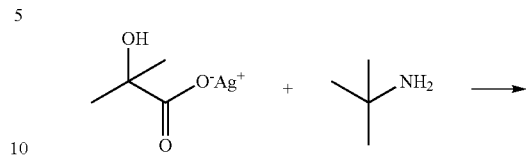

To a slurry of silver 2-hydroxybutyrate (1.0 g, 4.76 mmol) in acetonitrile (4 ml), t-butylamine (2.1 g, 30 mmol) was added to obtain a clear reaction solution. The reaction solution was stirred at 25° C. for 10 minutes and then the acetonitrile was slowly removed at room temperature to obtain a white solid of the desired silver 2-hydroxyisobutyrate t-butylamine complex as confirmed by crystal structure (see FIG. 1) and $^1$H NMR ($CD_3CN$).

Inventive Example 5: Preparation of Silver 2-Ethyl-2-Hydroxyisobutyrate Tert-Butylamine Complex

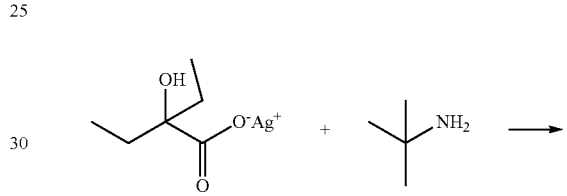

Figure 2:
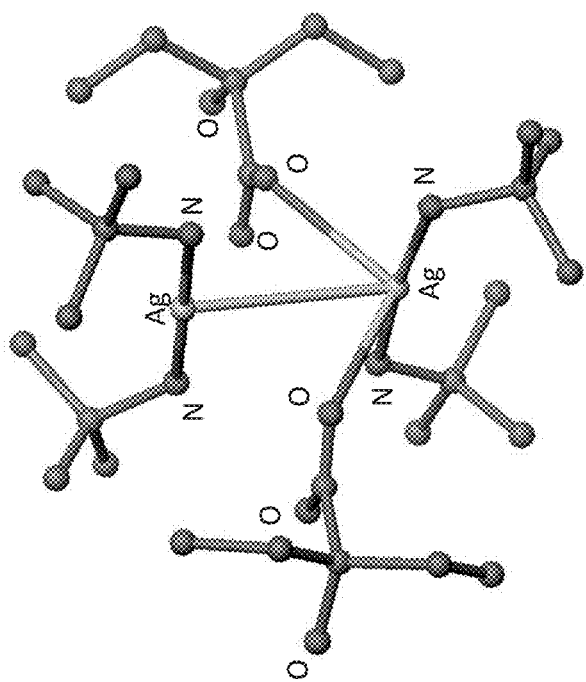
FIG. 2 is an illustration of the crystal structure of a silver ion-containing complex as described in Invention Example 5 below.

To a slurry of silver 2-ethyl-2-hydroxybutyrate (1.0 g, 4.76 mmol) in acetonitrile (4 ml), t-butylamine (0.7 g, 10 mmol) was added to obtain a clear reaction solution. The reaction solution was stirred at 25° C. for 10 minutes and then the acetonitrile was slowly removed at room temperature to obtain a white solid of the desired silver 2-hydroxyisobutyrate t-butylamine complex as confirmed by crystal structure (see FIG. 2) and $^1$H NMR ($CD_3CN$).

Inventive Example 6: Preparation of Silver Lactate 2,2,2-Trifluoroethylamine Complex

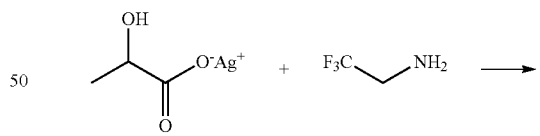

To a slurry of silver lactate (1.0 g, 5.076 mmol) in acetonitrile (4 ml), 2,2,2-trifluoroethyl amine (0.50 g, 5.08 mmol) was added to obtain a clear reaction solution. The reaction solution was stirred at 25° C. for 10 minutes and then the acetonitrile was slowly removed at room temperature to obtain a white solid of the desired silver lactate 2,2,2-trifluoroethylamine complex as confirmed by $^1$H NMR ($CD_3CN$).

Inventive Example 7: Electrochemical Characterization of Silver-Ion Complexes

The electrochemical properties of various silver-containing complexes as defined above using formula (I) were assessed by the common method of cyclic voltammetry as described for example in "Electrochemical Methods, Fundamentals and Applications," A. Bard and L. Faulkner (Editors), John Wiley & Sons, Inc. NY (1980). In this method, each complex was dissolved at a concentration of from about 1 to about 5 mmol in acetonitrile solvent containing 0.1 molar tetrabutylammonium-tetrafluoroborate as an electrolyte. Cyclic voltammetry was performed in a two-compartment glass cell equipped with a glassy carbon working electrode, a platinum counter electrode, and a saturated calomel (SCE) reference electrode. The SCE was separated from the main compartment of the cell by a salt bridge filled with 0.1 molar tetrabutylammonium-tetrafluoroborate electrolyte. The glassy carbon electrode was polished using 1 μm alumina paste prior to each voltammetric scan. Measurements were conducted at 25° C. using a potential sweep rate of 0.1 V/sec.

Figure 3:
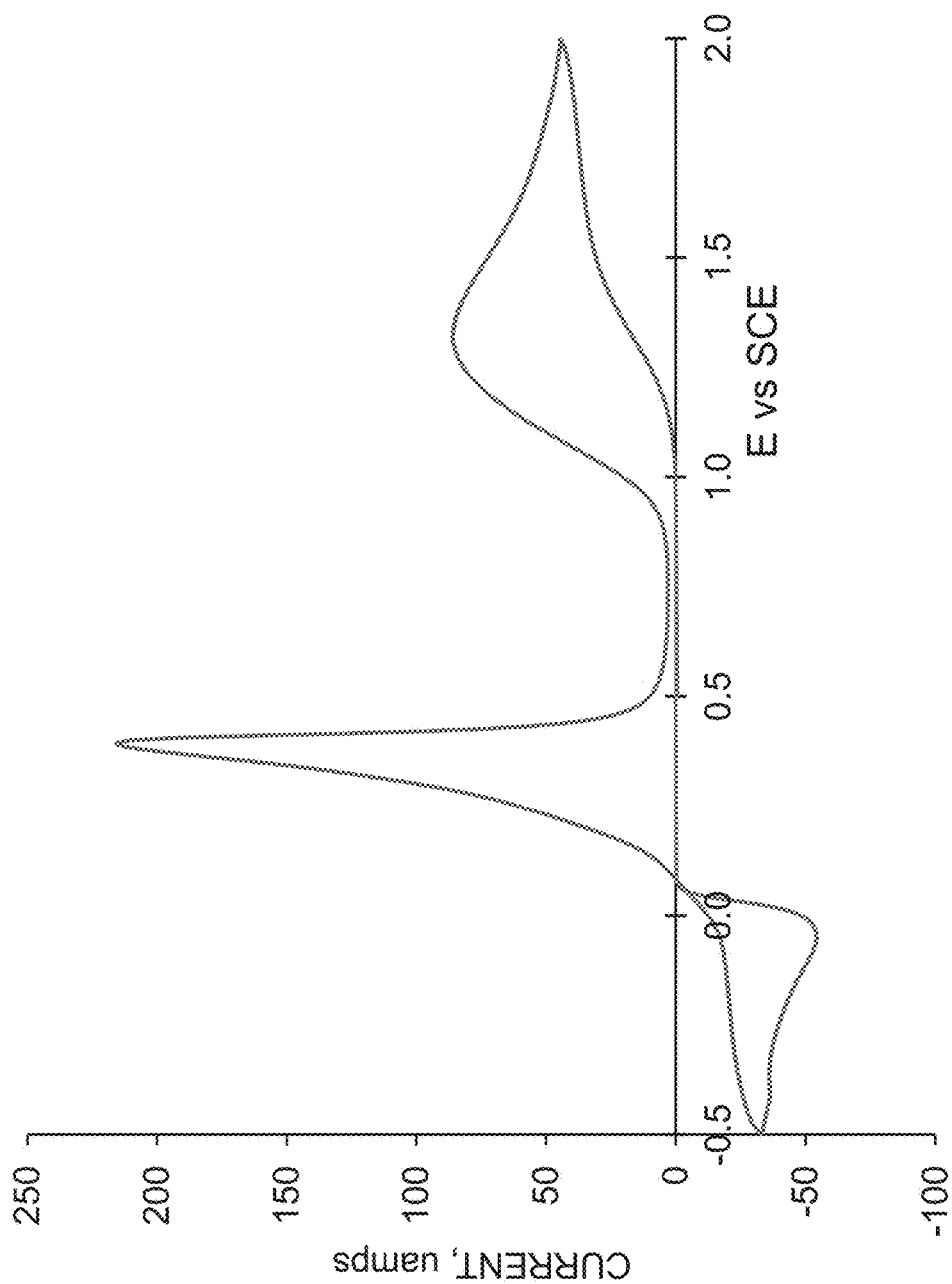
FIG. 3 is a graphical representation of a typical cyclic voltammogram of a silver ion-containing complex as described in Inventive Example 7 below.

A typical cyclic voltammogram of the silver lactate tert-butylamine complex prepared in Inventive Example 2 is shown in FIG. 3 wherein, the electrode potential is cycled between the limits of −0.5 V and +2.0 V starting in a negative-going direction from an initial potential of +0.5 V. Three electrochemically active regions were identified. The observed current "wave" in the negative potential region from +0.1 V to −0.5 V is associated with the electrochemical reduction of the silver ion-containing complex. This reduction process results in the plating of silver metal onto the carbon electrode. The sharp current wave observed in the positive potential region from +0.1 V to +0.5 V corresponds to the oxidation of the plated silver metal to form soluble silver ion. The sharp symmetrical shape of the latter electrochemical oxidation wave is fully consistent with the oxidation dissolution ("stripping") of silver metal from the electrode surface. Finally, a third, broad electrochemical wave in the positive potential region from about +1.0 V to +2.0 V (vs. SCE) is assigned to the overlapping oxidation waves of the incorporated component parts ("P" and "L") of the complex.

Cyclic voltammograms for other complexes of formula (I) are very similar to that of FIG. 3 Peak potentials for the reduction and oxidation of various complexes are shown in TABLE III below. Oxidation potentials determined for the individual α-oxy carboxylate components determined by the experimental method described above are shown in the following TABLE IV. Oxidation potentials for primary alkylamines are found for example in Adenier et al., Langmuir, 2004, Vol. 20, pp. 8243-8253.

TABLE III

Voltammetry Results for (Ag+)a(L)b(P)c in Acetonitrile

| Complex | L | P | Structure | Reduction peak Potential | Oxidation peak Potential |
|---|---|---|---|---|---|
| Inventive Example 2 | lactate | t-butyl amine | (structure) | −0.039 V | +1.31 V |

TABLE III-continued

Voltammetry Results for (Ag+)a(L)b(P)c in Acetonitrile

| Complex | L | P | Structure | Reduction peak Potential | Oxidation peak Potential |
|---|---|---|---|---|---|
| Inventive Example 6 | lactate | trifluoro-ethyl-amine | (structure) | +0.056 V | +1.20 V |

TABLE IV

Voltammetry Results for Carboxylate Components in Acetonitrile

| L | Oxidation Peak Potential |
|---|---|
| lactate | +1.1 V |
| acetate | +1.27 V |

Inventive Example 8: Printing and Photochemical Generation of Conductive Silver Metal Using Silver Lactate Tert-Butylamine Complex and a Mixture of PS-4 and PS-12 Photosensitizers This example demonstrates the photochemical generation of electrically-conductive silver metal in precursor articles to provide product articles comprising a polymeric substrate using a mixture of acridinium and coumarin class of photosensitizers.

This example demonstrates the preparation of precursor articles according to the present invention using flexographic printing and a silver ion-containing complex described below. It also demonstrates the photochemical generation, using the coumarin class of electron donor photosensitizers, of electrically-conductive silver metal to provide product articles comprising polymeric substrates.

A flexographic printing plate was obtained from a commercially available Kodak Flexcel NX photopolymer plate (precursor) using a flexographic IGT F1 printer. A relief image was provided by imaging the photopolymer plate through a mask that was written using the Kodak Square Spot laser technology at a resolution of 12,800 dpi. Exposure was carried out using a Fusion benchtop conveyor unit equipped with an H-bulb at a nominal UV dose of 500-1000 mJ/cm$^2$.

A photosensitive composition comprising 40 weight % solution of silver lactate tert-butylamine complex (from Inventive Example 2) in a mixture of acetonitrile-benzonitrile (85:15 v/v) solvent mixture along with 0.5 weight % of PS-4 and 1.5 weight % of PS-12 photosensitizers, was flexographically printed onto samples of a gelatin-subbed poly(ethylene terephthalate) (PET) film substrate to provide precursor articles having photosensitive thin film patterns on the substrate. The precursor articles were exposed to UV light to obtain thin film silver metal patterns. The resulting product articles were contacted with a sodium chloride solution (0.1-0.2 molar) and air dried before measuring the sheet resistivity. The resistivity measured by a four-point probe for the product articles over a 0.5×1.5 cm area and nominal thickness of 400 nm was found to be 10-15 Ω/□.

Inventive Example 9: Photochemical Generation of Conductive Silver Metal Using Silver 2-Hydroxy Isobutyrate Tert-Amylamine Complex and PS-15 Photosensitizer This example illustrates the photochemical generation of an electrically-conductive silver metal thin film on a glass substrate using inventive complexes and compositions.

A photosensitive reducible silver ion-containing composition comprising a 40 weight % solution of silver 2-hydroxy isobutyrate tert-amylamine in a mixture of acetonitrile solvent and 2 weight % of PS-15 photosensitizer, was spin coated onto a glass plate and the resulting precursor article was exposed to UV light to obtain a thin film silver metal coating. The product article was contacted with sodium chloride solution (0.1-0.2 molar) and air dried before measuring the sheet resistivity. The resistivity measured by a four-point probe for the films with a 1 cm² area and nominal thickness of 300 nm was found to be 10-20 Ω/□.

The invention has been described in detail with particular reference to certain preferred embodiments thereof, but it will be understood that variations and modifications can be effected within the spirit and scope of the invention.

The invention claimed is:

1. A non-hydroxylic-solvent soluble silver complex comprising: a reducible silver ion complexed with an α-oxy carboxylate and a primary alkylamine, the non-hydroxylic-solvent soluble silver complex being represented by the following formula (I):

$$(Ag^+)_a(L)_b(P)_c \quad (I)$$

wherein L represents the α-oxy carboxylate; P represents the primary alkylamine; a is 1 or 2; b is 1 or 2; and c is 1, 2, 3, or 4, provided that when a is 1, b is 1, and when a is 2, b is 2.

2. The non-hydroxylic-solvent soluble silver complex of claim 1, wherein L is represented by the following formula (II):

wherein $R_1$, $R_2$, and $R_3$ are independently hydrogen or linear or branched alkyl groups.

3. The non-hydroxylic-solvent soluble silver complex of claim 2, wherein $R_1$ is hydrogen or a branched or linear alkyl group having 1 to 3 carbon atoms, and $R_2$ and $R_3$ are independently branched or linear alkyl groups having 1 to 8 carbon atoms, wherein any of the hydrogen atoms in the $R_1$, $R_2$, and $R_3$ branched or linear alkyl groups optionally can be replaced with a fluorine atom.

4. The non-hydroxylic-solvent soluble silver complex of claim 1, wherein the α-oxy carboxylate has a molecular weight of 250 or less.

5. The non-hydroxylic-solvent soluble silver complex of claim 1, wherein L is represented by the following formula (III):

wherein $R_4$ is a branched or linear alkyl group having 1 to 8 carbon atoms and any of the hydrogen atoms in the $R_4$ branched or linear alkyl group optionally can be substituted with a fluorine atom.

6. The non-hydroxylic-solvent soluble silver complex of claim 1, wherein the α-oxy carboxylate is selected from the group consisting of lactate, 2-hydroxybutyric acid, 2-hydroxy-3-methylbutyric acid, 2-hydroxy-3,3-dimethylbutyric acid, 2-hydroxy-isobutyric acid, 2-hydroxy-2-methylbutyric acid, 2-ethyl-2-hydroxybutyric acid, 2-hydroxy-2,3-dimethylbutyric acid, 2-ethyl-2-methoxybutyric acid, 2-methoxy-2-methylpropanoic acid, 1-hydroxycyclopentane-1-carboxylic acid, 2,3-dihydroxy-2,3-dimethylsuccinic acid, and 2,4-dihydroxy-2,4-dimethylpentanedioic acid, or
  selected from the group consisting of pyruvic acid, 3-methylpyruvic acid, 3,3-dimethylpyruvic acid, 3,3-dimethyl-2-oxobutanoic acid, 3,3-dimethyl-2-oxopentanoic acid, and 2,3-dioxosuccinic acid.

7. The non-hydroxylic-solvent soluble silver complex of claim 1, wherein P is a primary alkylamine having a boiling point of less than or equal to 175° C.

8. The non-hydroxylic-solvent soluble silver complex of claim 1, wherein P is a primary alkylamine having a boiling point of less than or equal to 125° C.

9. The non-hydroxylic-solvent soluble silver complex of claim 1, wherein the primary alkylamine has an oxidation potential of greater than 1.0 V vs. SCE; the α-oxy carboxylate has a first oxidation potential of at least 1.2 V vs. SCE; and upon decarboxylation of the α-oxy carboxylate, a second radical is generated that has an oxidation potential of less than 1.0 V vs. SCE.

10. The non-hydroxylic-solvent soluble silver complex of claim 1, wherein the primary alkylamine has an oxidation potential of greater than 1.4 V vs. SCE.

11. The non-hydroxylic-solvent soluble silver complex of claim 1, wherein the primary alkylamine has a pKa of at least 1 and up to and including 30 as measured in acetonitrile.

12. The non-hydroxylic-solvent soluble silver complex of claim 1, wherein the primary alkylamine has a pKa of at least 10 and up to and including 25 as measured in acetonitrile, and the primary alkylamine has an oxidation potential that is greater than 1.0 V vs. SCE.

13. The non-hydroxylic-solvent soluble silver complex of claim 1, wherein the primary alkylamine comprises a branched or linear alkyl group having 3 to 6 carbon atoms.

14. The non-hydroxylic-solvent soluble silver complex of claim 1, wherein the primary alkylamine is selected from the group consisting of propylamine, n-butylamine, t-butylamine, isopropylamine, 2,2,2-trifluoroethylamine, 2,2,3-pentafluoropropylamine, 3,3,3-trifluoropropylamine, 1,2-dimethylpropylamine, t-amyl amine, isopentylamine, 2-amino-3-methylbutane, 3,3-dimethyl-2-butylamine, 2-aminohexane, and sec-butylamine.

15. The non-hydroxylic-solvent soluble silver complex of claim 1, which meets a silver ion stability test such that when the non-hydroxylic-solvent soluble silver complex is held for 24 hours at ambient temperature and under yellow safelight, less than 0.1 mol % of its original silver ion content is reduced to silver metal.

16. The non-hydroxylic-solvent soluble silver complex of claim 1, wherein:

L has a molecular weight of 250 or less, and L is represented by either the following formula (II) or (III):

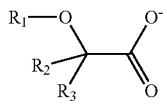
(II)

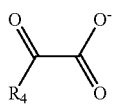
(III)

wherein $R_1$ is hydrogen or an alkyl group having 1 or 2 carbon atoms, $R_2$ and $R_3$ are independently branched or linear alkyl groups having 1 to 8 carbon atoms, wherein any of the hydrogen atoms in the $R_1$, $R_2$, and $R_3$ branched or linear alkyl groups optionally can be replaced with a fluorine atom, and $R_4$ is a branched or linear alkyl group having 1 to 8 carbon atoms wherein any of the hydrogen atoms optionally can be replaced with a fluorine atom; and P is a primary alkylamine that is selected from the group consisting of propylamine, n-butylamine, t-butylamine, isopropylamine, 2,2,2-trifluoroethylamine, 2,2,3,3,3-pentafluoropropylamine, 3,3,3-trifluoropropylamine, 1,2-dimethylpropylamine, t-amyl amine, isopentylamine, 2-amino-3-methylbutane, 3,3-dimethyl-2-butylamine, 2-aminohexane, and sec-butylamine.

17. The non-hydroxylic-solvent soluble silver complex of claim 1, wherein:

(i) a and b are both 1 and c is 1 or 2;
(ii) a and b are both 2 and c is 2; or
(iii) a and b are both 2 and c is 4.

* * * * *